United States Patent
Hanna et al.

(10) Patent No.: US 8,242,243 B2
(45) Date of Patent: Aug. 14, 2012

(54) METHODS AND REAGENTS FOR DETECTING CPG METHYLATION WITH A METHYL CPG BINDING PROTEIN (MBP)

(75) Inventors: Michelle M. Hanna, Carlsbad, CA (US); David McCarthy, Carlsbad, CA (US)

(73) Assignee: RiboMed Biotechnologies, Inc., San Diego, CA (US)

(*) Notice: Subject to any disclaimer, the term of this patent is extended or adjusted under 35 U.S.C. 154(b) by 83 days.

(21) Appl. No.: 12/467,246

(22) Filed: May 15, 2009

(65) Prior Publication Data

US 2009/0298080 A1   Dec. 3, 2009

Related U.S. Application Data

(60) Provisional application No. 61/053,648, filed on May 15, 2008.

(51) Int. Cl.
*C07K 1/00* (2006.01)
*C12Q 1/68* (2006.01)

(52) U.S. Cl. .......................... 530/350; 435/6.1

(58) Field of Classification Search .................. None
See application file for complete search history.

(56) References Cited

U.S. PATENT DOCUMENTS

| | | |
|---|---|---|
| 3,996,345 A | 12/1976 | Ullman et al. |
| 4,351,760 A | 9/1982 | Khanna et al. |
| 4,582,788 A | 4/1986 | Erlich |
| 4,683,194 A | 7/1987 | Saiki |
| 4,739,044 A | 4/1988 | Stabinsky |
| 4,757,141 A | 7/1988 | Fung |
| 4,786,600 A | 11/1988 | Kramer et al. |
| 5,130,238 A | 7/1992 | Malek et al. |
| 5,169,766 A | 12/1992 | Schuster et al. |
| 5,194,370 A | 3/1993 | Berninger et al. |
| 5,215,899 A | 6/1993 | Dattagupta |
| 5,246,866 A | 9/1993 | Nasu et al. |
| 5,399,491 A | 3/1995 | Kacian et al. |
| 5,503,979 A | 4/1996 | Kramer et al. |
| 5,508,178 A | 4/1996 | Rose et al. |
| 5,554,516 A | 9/1996 | Kacian et al. |
| 5,571,669 A | 11/1996 | Lu et al. |

(Continued)

FOREIGN PATENT DOCUMENTS

EP    0369775    5/1990

(Continued)

OTHER PUBLICATIONS

D3QW01 (last viewed on Sep. 6, 2011).*

(Continued)

*Primary Examiner* — Alexander Kim
(74) *Attorney, Agent, or Firm* — The Law Office of Jane K. Babin, Professional Corporation; Jane K. Babin

(57) ABSTRACT

The present invention provides a simple and sensitive technology for the detection of CpG methylation in DNA without chemical modification of sample DNA by bisulfite treatment or PCR amplification. Signal generation is based on an Abscription (Abortive Transcription) technology in which DNA signal generators called Abortive Promoter Cassettes (APCs) are bound to target mCpG sites via mCpG target specific probes based on methyl binding polypeptides or methyl binding domains thereof. RNA polymerase produces uniform, short RNA molecules from synthetic promoters in APCs as signals of the presence of methylated CpGs. Detection of CpG methylation and hypermethylation of DNA targets such as CpG islands provides a convenient means for detecting and monitoring cancer in a subject.

20 Claims, 10 Drawing Sheets

U.S. PATENT DOCUMENTS

| | | | |
|---|---|---|---|
| 5,595,891 A | 1/1997 | Rose et al. | |
| 5,597,694 A | 1/1997 | Munroe et al. | |
| 5,648,211 A | 7/1997 | Fraiser et al. | |
| 5,654,142 A | 8/1997 | Kievits et al. | |
| 5,654,176 A | 8/1997 | Smith | |
| 5,679,512 A | 10/1997 | Laney et al. | |
| 5,683,879 A | 11/1997 | Laney et al. | |
| 5,744,308 A | 4/1998 | Guillou-Bonnici et al. | |
| 5,766,849 A | 6/1998 | McDonough et al. | |
| 5,786,462 A | 7/1998 | Schneider et al. | |
| 5,824,517 A | 10/1998 | Cleuziat et al. | |
| 5,837,459 A | 11/1998 | Berg et al. | |
| 5,846,723 A | 12/1998 | Kim et al. | |
| 5,849,723 A | 12/1998 | Phillion et al. | |
| 5,858,801 A | 1/1999 | Brizzolara | |
| 5,888,729 A | 3/1999 | Kacian et al. | |
| 5,888,819 A | 3/1999 | Goelet et al. | |
| 5,912,340 A | 6/1999 | Kutyavin et al. | |
| 6,008,334 A | 12/1999 | Hanna | |
| 6,107,037 A | 8/2000 | Sousa et al. | |
| 6,107,039 A | 8/2000 | Hanna et al. | |
| 6,114,519 A | 9/2000 | Cole | |
| 6,251,594 B1 | 6/2001 | Gonzalgo et al. | |
| 6,268,131 B1 | 7/2001 | Kang et al. | |
| 7,045,319 B2 * | 5/2006 | Hanna | 435/91.1 |
| 7,226,738 B2 | 6/2007 | Hanna | |
| 7,468,261 B2 * | 12/2008 | Hanna | 435/91.1 |
| 7,470,511 B2 * | 12/2008 | Hanna | 435/6.15 |
| 7,473,775 B2 * | 1/2009 | Hanna | 536/24.33 |
| 7,541,165 B2 | 6/2009 | Hanna | |
| 2002/0168641 A1 | 11/2002 | Mortensen et al. | |
| 2003/0099950 A1 | 5/2003 | Hanna | |
| 2003/0138783 A1 | 7/2003 | Sukumar et al. | |
| 2004/0054162 A1 | 3/2004 | Hanna | |
| 2004/0157257 A1 * | 8/2004 | Hanna | 435/6 |
| 2004/0175724 A1 | 9/2004 | Hanna | |
| 2005/0214796 A1 | 9/2005 | Hanna | |
| 2006/0204964 A1 | 9/2006 | Hanna | |
| 2006/0240460 A1 | 10/2006 | Pfeiffer et al. | |
| 2006/0269937 A1 | 11/2006 | Clark et al. | |
| 2007/0026393 A1 | 2/2007 | Berlin et al. | |
| 2008/0124716 A1 | 5/2008 | Cooney et al. | |

FOREIGN PATENT DOCUMENTS

| | | |
|---|---|---|
| EP | 1364069 | 4/2009 |
| WO | 8901050 | 2/1989 |
| WO | 9641006 | 12/1996 |
| WO | 0125485 A2 | 4/2001 |
| WO | 03014388 | 2/2003 |
| WO | 03038042 A2 | 5/2003 |
| WO | 03044226 | 5/2003 |
| WO | 03038042 A3 | 3/2004 |
| WO | 2004096997 A2 | 11/2004 |
| WO | 2009140666 A2 | 11/2009 |
| WO | 2009140666 A3 | 11/2009 |
| WO | 2010009060 A2 | 1/2010 |
| WO | 2010009060 A3 | 6/2010 |
| WO | 2010107716 A2 | 9/2010 |
| WO | 2010107716 A3 | 3/2011 |

OTHER PUBLICATIONS

P0A9D2 (last viewed on Sep. 6, 2011).*

Nan et al., Dissection of the methyl-CpG binding domain from the chromosomal protein MeCP2, Nucleic Acid Research, 1993, vol. 21, pp. 4886-4892.*

Hendrich et al., Identification and Characterization of a Family of Mammalian Methyl-CpG Binding Proteins, Mol Cell Biol. Nov. 1998; vol. 18(11), pp. 6538-6547.*

Berg et al., Ten members of the *Arabidopsis* gene family encoding methyl-CpG-binding domain proteins are transcriptionally active and at least one, AtMBD11, is crucial for normal development., Nucleic Acids Research, 2003, vol. 31, pp. 5291-5304.*

"AluI Methyltransferase", New England Biolabs online catalog (viewed at http://www.neb.com/nebecomm/products/productM0220.asp on Jan. 14, 2012).

"Cloning vector pBR322, complete sequence", GenBank; Accession No. J01749; GI: 208958, Sep. 30, 2008, pp. 1-7.

"CpG site", Wikipedia, viewed at http://en.wikipedia.org/wiki/CpG_site, Jan. 16, 2012.

"Dam and Dcm Methylases of *E. coli*", (viewed at http://www.neb.com/nebecomm/tech_reference/restriction_enzymes/dam_dcm_methylases_of_ecoli.asp on Jan. 14, 2012).

"Demethylase", Wikipedia (viewed at http://en.wikipedia.org/wiki/Demethylase on Jan. 16, 2012).

"EcoRI Methyltransferase", New England Biolabs online catalog (viewed at http://www.neb.com/nebecomm/products/productM0211.asp on Jan. 14, 2012).

"Glutathione S-transferase", Wikipedia (viewed at http://en.wikipedia.org/wiki/Glutathione_S-transferase on Dec. 17, 2011).

"GST Gene Fusion System Handbook", GE Healthcare, 18-1157-58 AB (downloaded from http://www.gelifesciences.com/aptrix/upp01077.nsf/Content/Products?OpenDocument&parentid=976038&moduleid=164393&zone=Proteomics on Dec. 17, 2011).

"HaeIII Methyltransferase", New England Biolabs online catalog (viewed at http://www.neb.com/nebecomm/ products/productM0224.asp on Jan. 14, 2012).

"MBD2", HUGO Gene Nomenclature Committee Report on (viewed at http://www.genenames.org/data/hgnc_data.php?hgnc_id=6990 on Dec. 17, 2011).

"MBD2", National Center for Biotechnology Information Gene Report (viewed at http://www.ncbi.nlm.nih.gov/gene/8932 on Dec. 17, 2011).

"MECP2", HUGO Gene Nomenclature Committee Report (viewed at http://www.genenames.org/data/hgnc_data.php?hgnc_id=6990 on Dec. 17, 2011).

"MeCP2", National Center for Biotechnology Gene Report for MECP2 (viewed at http://www.ncbi.nlm.nih.gov/gene/4204 on Dec. 17, 2011).

"MECP2", Wikipedia (viewed at http://en.wikipedia.org/wiki/MECP2 on Dec. 17, 2011).

"Methyl CpG binding protein 2 (Rett syndrome) (MECP2)", UniGene (viewed at http://www.ncbi.nlm.nih.gov/UniGene/clust.cgi?ORG=Hs&CID=200716&ALLPROT=1 on Jan. 16, 2012).

"Methyl-CpG binding domain protein 1 (MBD1)", UniGene (viewed at http://www.ncbi.nlm.nih.gov/UniGene/clust.cgi?ORG=Hs&CID=405610&ALLPROT=1on Jan. 16, 2012).

"Methyl-CpG binding domain protein 2 (MBD2)", , UniGene (viewed at http://www.ncbi.nlm.nih.gov/UniGene/clust.cgi?ORG=Hs&CID=25674&ALLPROT=1 on Jan. 16, 2012).

"Methyl-CpG binding domain protein 4 (MBD4)", UniGene (viewed at http://www.ncbi.nlm.nih.gov/UniGene/clust.cgi?ORG=Hs&CID=35947&ALLPROT=1 on Jan. 16, 2012).

"Methyl-CpG-binding domain protein 2", Wikipedia (viewed at http://en.wikipedia.org/wiki/MBD2on Dec. 17, 2011).

"Methyl-CpG-Binding Domain Protein 2; MBD2", OMIM 603547 (Online Mendelian Inheritance in Man, entry 603547, viewed at http://omim.org/entry/603547 on Dec. 17, 2011).

"Methyl-CpG-Binding Protein 2; MECP2", OMIM 300005 viewed at http://omim.org/entry/300005, Dec. 17, 2011.

"Methytransferase", Wikipedia (viewed at http://en.wikipedia.org/wiki/Methyltransferase on Dec. 16, 2011).

"Protein Domain", Wikipedia (viewed at http://en.wikipedia.org/wiki/Protein_domain on Dec. 17, 2011).

"UniGene Homepage", UniGene (viewed at http://www.ncbi.nlm.nih.gov/unigene on Jan. 16, 2012).

Adorjan et al., "Tumour class prediction and discovery by microarray-based DNA methylation analysis", Nucleic Acids Res. 30: e21, 2002.

Agrawal et al., "Site-specific functionalization of oligodeoxynucleotides for attaching two different reporter groups", Nucleic Acids Res. 18, 1990, 5419-5423.

Aiyar et al., "A Mismatch Bubble in Double-stranded DNA Suffices to Direct Precise Transcription Initiation by *Escherichia coli* RNA Polymerase", J. Biol. Chem. vol. 269, No. 18, 1994, 13179-131.

Akiyama et al., "Cell-Type-Specific Repression of the Maspin Gene Is Disrupted Frequently by Demethylation at the Promoter Region in Gastric Intestinal Metaplasia and Cancer Cells", Am J Pathology, vol. 163, No. 5, 2003, 1911-1919.

Alaminos et al., "Clustering of Gene Hypermethylation Associated With Clinical Risk Groups in Neuroblastoma.", Journal of the National Cancer Institute, vol. 96, No. 16, 2004, 1208-19.

Antequera et al., "Number of CpG islands and genes in human and mouse", Proc. Natl. Acad. Sci. USA, vol. 90, 1993, 11995-11999.

Badal et al., "CpG Methylation of Human Papillomavirus Type 16 DNA in Cervical Cancer Cell Lines and in Clinical Specimens: Genomic Hypomethylation Correlates with Carcinogenic Progression", Journal of Virology, vol. 77 No. 11, 2003, 6227-6234.

Ballestar et al., "Methyl-CpG-binding proteins Targeting specific gene repression", Eur. J. Biochem. 268, 2001, 1-6.

Barletta et al., "Reversal of loss of imprinting in tumor cells by 5-aza-2'-deoxycytidine.", Cancer Res 57, 1997, 48-50.

Belinsky et al., "Aberrant CpG island methylation of the $p^{16INK4a}$ and estrogen receptor genes in rat lung tumors induced by particulate carcinogens" Carcinogenesis vol. 23, No. 2, 2002, 335-9.

Belinsky et al., "Promoter hypermethylation of multiple genes in sputum precedes lung cancer incidence in a high-risk cohort", Cancer Res 66:(6), 2006, 3338-44.

Bhattacharya et al., "A mammalian protein with specifc demethylase activity for mCpG DNA", Nature 397, 1999, 579-83.

Boeke et al., "The Minimal Repression Domain of MBD2b Overlaps with the Methyl-CpG-binding Domain and Binds Directly to Sin3A", Journal of Biological Chemistry, vol. 275, No. 45, 2000, 34963-7.

Brock et al., "Prognostic importance of promoter hypermethylation of multiple genes in esophageal adenocarcinoma[1]", Clinical Cancer Research, vol. 9, 2003, 2912-9.

Cairns et al., "Molecular detection of prostate cancer in urine by GSTP1 hypermethylation[1]", Clinical Cancer Research, vol. 7, 2001, 2727-30.

Callahan et al., "Frequent Mutations in Breast Cancer", Ann. N.Y. Acad. Sci. 698, 1993, 21-30.

Chamberlin, "Bacterial DNA-Dependent RNA Polymerases", in The Enzymes, Boyer P.D., ed. Academic Press, New York, N.Y., 1982, 61, 84-86.

Chan et al., "Hypermethylation of multiple genes in tumor tissues and voided urine in urinary bladder cancer patients", Clinical Cancer Research 8, 2002, 464-70.

Cheng et al., "Inhibition of DNA Methylation and Reactivation of Silenced Genes by Zebularine", Journal of the National Cancer Inst. vol. 95, No. 5, 2003, 399-409.

Cheung et al., "A Resource of Mapped Human Bacterial Artificial Chromosome Clones", Genome Research, 1999, 983-993.

Cho et al., "Hypomethylation of the MN/CA9 promoter and upregulated MN/CA9 expression in human renal cell carcinoma.", Br J Cancer 85, 2001, 563-7.

Christmann et al., "Acquired resistance of melanoma cells to the antineoplastic agent fotemustine is caused by reactivation of the DNA repair gene MGMT.", Int J Cancer 92, M, 2001, 123-9.

Cifone et al., "Increasing metastatic potential is associated with increasing genetic instability of clones isolated from murine neoplasms", Proc. Natl. Acad. Sci. USA 78, 1981, 6949-6952.

Clarke et al., "S-Adenosylmethionine-Dependent Methyltransferases", in Homocysteine in Health and Disease, Carmel & Jacobsen, eds (Cambridge University Press)., 2001, 63-78.

Claus et al., "Epigenetic targets in hematopoietic malignancies.", Oncogene 22, 2003, 6489-96.

Costas et al., "RNA-protein crosslinking to AMP residues at internal positions in RNA with a new photocrosslinking ATP analog", Nucleic Acids Res. 23, 2000, 1849-1858.

Cunningham et al., "Hypermethylation of the hMLH1 promoter in colon cancer with microsatellite instability", Cancer Res 58, 1998, 3455-60.

Daube et al., "Coupling of RNA displacement and intrinsic termination in transcription from synthetic RNA DNA bubble duplex constructs", Proc. Natl Acad. Set USA 91, 1994, 9539-9543.

Daube et al., "Functional Transcription Elongation Complexes from Synthetic RNA-DNA Bubble Duplexes", Science 258, 1992, 1320-1324.

De Smet et al., "The activation of human gene MAGE-1 in tumor cells is correlated with genome-wide demethylation.", Proc Natl Acad Sci U S A93:, 1996, 7149-53.

Deitch, et al., "Promoter-specific Activation and Demethylation by MBD2/Demethylase", J Biol Chem. 277, 2002, 35791-4.

Dhasarathy et al., "The MBD protein family—reading an epigenetic mark?", Mutat Res. 647, 2008, 39-43.

Dissinger et al., "Active site labeling of *Escherichia coli* transcription elongation complexes with 5-[4-azidophenacyl)thio)uridine 5'-triphosphate", J Biol Chem 265, S, 1990, 7662-8.

Dulaimi et al., "Clin Cancer Res 10", Detection of bladder cancer in urine by a tumor suppressor gene hypermethylation panel, 2004, 1887-93.

Dunn et al., "Complete Nucleotide Sequence of Bacteriophage T7 DNA and the Locations of T7 Genetic Elements", J. Mol. Biol. 166, 1982, 477-535.

Eads et al., "MethyLight: a high-throughput assay to measure DNA methylation", Nucleic Acids Res 28, 2000, e32.

Enrich et al., "A new method for accurate assessment of DNA quality after bisulfite treatment", Nucleic Acids Res 35, 2007, e29.

Esteller et al., "A gene hypermethylation profile of human cancer", Cancer Res 61, 2001, 3225-9.

Esteller, "CpG island hypermethylation and tumor suppressor genes: a booming present, a brighter future.", Oncogene 21, 2002, 5427-40.

Esteller et al., "Hypermethylation-associated Inactivation of the Cellular Retinol-Binding-Protein 1 Gene in Human Cancer", Cancer Res 62, 2002, 5902-5.

Esteller et al., "Promoter Hypermethylation and BRCA1 inaccivation in Sporadic Breast and Ovarian Tumors", J. Natl. Cancer Inst. 52, 2000, 564-569.

Fraga et al., "The affnity of different MBD proteins for a specifc methylated locus depends on their intrinsic binding properties", Nucl. Acids Res, 31, 2003, 1765-1774.

Frommer et al., "A genomic sequencing protocol that yields a positive display of 5-methylcytosine residues in individual DNA strands", Proc. Natl Acad. Sci. USA 39, 1992, 1827-1831.

Gait, "An Introduction to Modern Methods of DNA Synthesis", in Oligonucleotide synthesis: a practical approach, Gait, M.J., ed., Oxford University Press, Oxford, Great Britain, 1984, 1-22.

Gait et al., "Oligoribonucleotide synthesis", in Oligonucleotides and Analogues, 1992, 25-31.

Gama-Sosa et al., "The 5-methylcytosine content of DNA from human tumors", Nucleic Acids Res vol. 11, No. 19, 1983, 6883-94.

Gebhard et al., "Rapid and sensitive detection of CpG-methylation using methyl-binding (MB)-PCR.", Nucleic Acids Res vol. 34, No. 11, 2006, e82.

Geider et al., "An RNA transcribed from DNA at the origin of phage fd single strand to replicative form conversion", Proc. Natl. Acad. Sci. USA vol. 75, No. 2, 1978, 645-649.

Giusti et al., "Synthesis and Characterization of 5'-Fluorescent-dye-labeled Oligonucleotides", PCR Methods Appl. 2, 1993, 223-227.

Gonzalez-Zulueta et al., "Methylation of the 5' CpG island of the p16/CDKN2 tumor suppressor gene in normal and transformed human tissues correlates with gene silencing", Cancer Res 55, 1995, 4531-5.

Gonzalgo et al., "Molecular profiling and classification of sporadic renal cell carcinoma by quantitative methylation analysis.", Clin Cancer Res 10, 2004, 7276-83.

Graff et al., "E-cadherin expression is silenced by DNA hypermethylation in human breast and prostate carcinomas", Cancer Res 55, 1995, 5195-9.

Graff et al., "Methylation patterns of the E-cadherin 5' CpG island are unstable and reflect the dynamic, heterogeneous loss of E-cadherin expression during metastatic progression.", J Biol Chem vol. 275, No. 4, 2000, 2727-32.

Graziano et al., "Prognostic analysis of E-cadherin gene promoter hypermethylation in patients with surgically resected, node-positive, diffuse gastric cancer.", Clin Cancer Res 10, 2784-9, (2004).

Guatelli et al., "Isothermal, in vitro amplification of nucleic acids by a multienzyme reaction modeled after retroviral replication", Proc. Natl. Acad. Sci. USA 87, 1990, 1874-1878.

Gupta et al., "A general method for the synthesis of 3'-sulfhydryl and phosphate group containing oligonucleotides", Nucleic Acids Res vol. 19, No. 11, 1991, 3019-3025.

Gurevich et al., "Preparative in Vitro mRNA Synthesis Using SP6 and T7 RNA Polymerases", Anal. Biochem. 195, 1991, 207-213.

Hanna, "Photoaffinity Cross-Linking Methods for Studying RNA-Protein Interactions", Methods Enzymol. 180, 1989, 383-409.

Hanna et al., "Probing the environment of nascent RNA in *Escherichia coli* transcription elongation complexes utilizing a new fluorescent ribonucleotide analog", Nucleic Acids Res 27, 1999, 1369-1376.

Hanna et al., "Synthesis and characterization of a new photocrosslinking CTP analog and its use in photoaffinity labeling *E.coli* and T7 RNA polymerases", Nucleic Acids Res vol. 21, No. 21, 1993, 2073-2079.

Hanna et al., "Topography of transcription: Path of the leading end of nascent RNA through the *Escherichia coli* transcription complex", Proc. Natl Acad. Sci. USA 80, 1983, 4238-4242.

He et al., "Preparation of probe-modified RNA with 5-mercapto-UTP for analysis of protein-RNA interactions", Nucleic Acids Res. vol. 23, No. 7, 1995, 1231-1238.

Herman et al., "Distinct patterns of inactivation of $p15^{INK4B}$ and $p16^{INK4A}$ characterize the major types of hematological malignancies", Cancer Res 57, 1997, 837-41.

Herman et al., "Inactivation of the CDKN2/p16/MTS1 Gene Is Frequently Associated with Aberrant DNA Methylation in AH Common Human Cancers", Cancer Res. 55, 1995, 4525-4530.

Herman et al., "Incidence and functional consequences of hMLH1 promoter hypermethylation in colorectal carcinoma", Proc. Natl. Acad Sci USA 35, 1998, 6870-6875.

Herman et al., "Methylation-specific PCR: a novel PCR assay for methylation status of CpG islands", Proc Natl Acad Sci U S A. 93, 1996, 9821-6.

Herman, "Silencing of the VHL tumor-suppressor gene by DNA methylation in renal carcinoma.", Proc Natl Acad Sci U S A 91, 1994, 9700-4.

Hoque et al., "Quantitation of promoter methylation of multiple genes in urine DNA and bladder cancer detection", J Natl Cancer Inst. 98, 2006, 996-1004.

Hoque et al., "Quantitative detection of promoter hypermethylation of multiple genes in the tumor, urine, and serum DNA of patients with renal cancer", Cancer Res 64, 2004, 5511-7.

Horii et al., "Frequent Replication Errors at Microsatellite Loci in Tumors of Patients with Multiple Primary Cancers", Cancer Res. 54, 1994, 3373-3375.

Iravani et al., "Methylation of the multi tumor suppressor gene-2 (MTS2, CDKN1, p15INK4B) in childhood acute lymphoblastic leukemia", Oncogene 15, 1997, 2609-14.

Issa et al., "Methylation of the oestrogen receptor CpG island links ageing and neoplasia in human colon", Nat. Genet. 7, 1994, 536-540.

Jahr et al., "DNA fragments in the blood plasma of cancer patients: quantitations and evidence for their origin from apoptotic and necrotic cells.", Cancer Res 61, 2001, 1659-65.

Jeronimo, "A quantitative promoter methylation profile of prostate cancer.", Clin Cancer Res 10, 2004, 8472-8.

Jin, "An *Escherichia coli* RNA Polymerase Defective in Transcription due to its Overproduction of Abortive Initiation Products", J. Mol. Biol-236, 1994, 72-80.

Kang et al., "CpG island methylation in premalignant stages of gastric carcinoma.", Cancer Res 61, 2001, 2847-51.

Kinsella et al., "RNA Polymerase: Correlation Between Transcript Length, Abortive Product Synthesis, and Formation of a Stable Ternary Complex", Biochemistry 27, 1982, 2719-2723.

Kwoh et al., "Transcription-based amplification system and detection of amplified human immunodeficiency virus type 1 with a bead-based sandwich hybridization format", Proc. Natl. Acad. Sci. USA 86, 1989, 1173-1177.

Langer et al., "Enzymatic synthesis of biotin-labeled polynucleotides: Novel nucleic acid affinity probes", Proc. Nad. Acad. Scl. USA vol. 78, No. 11, 1981, 6633-6637.

Lee et al., "Aberrant CpG island hypermethylation along multistep hepatocarcinogenesis.", Am J Pathol vol. 163, No. 4, 2003, 1371-8.

Lewis et al., "Transcription of Simian Virus 40 DNA by Wheat Germ RNA Polymerase II", J. Biol. Chem. 255, 1980, 4928-4936.

Lin et al., "Genome-wide hypomethylation in hepatocellular carcinogenesis", Cancer Res 61, 2001, 4238-43.

Loeb et al., "Mutator Phenotype May Be Required for Multistage Carcinogenesis", Cancer Res. 52, 1991, 3075-3079.

Mancini et al., "Constitutively Methylated CpG Dinucleotides as Mutation Hot Spots in the Retinoblastoma Gene (RB1)", Am J. Human Genet 61, 1997, 80-87.

Marras et al., "Genotyping single nucleotide polymorphisms with molecular beacons", In Kwok (ed), Single nucleotide polymophisms: methods and protocols. (The Human Press Inc., Totowa, NJ) vol. 212, 2003, 111-128.

Martin et al., "Processivity in Early Stages of Transcription by T7 RNA Polymerase", Biochemistry 27, 1988, 3966-3974.

Maruyama et al., "Aberrant promoter methylation profile of bladder cancer and its relationship to clinicopathological features", Cancer Res 61, 2001, 8659-63.

Meinkoth et al., "Hybridization of Nucleic Acids Immobilized on Solid Supports", Anal. Blochem. 138, 1984, 267-284.

Meyer et al., "Synthesis and Characterization of a New 5-Thiol-Protected Deoxyuridine Phosphoramidite for Site-Specific Modification of DNA", Bioconjugate Chem. 7, 1996, 401-412.

Milligan et al., "Synthesis of Small RNAs Using T7 RNA Polymerase", Methods Enzymol. 180, 1989, 51-62.

Montemagno et al., "Constructing nanomechanical devices powered by biomolecular motors", Nanotechnology 10, IOP Publishing Ltd., 1999, 225-231.

Mullis et al., "Specific Enzymatic Amplification of DNA in Vitro: The Polymerase Chain Reaction", Cold Spring Harb. Symp. Quant. Biol. 51, 1986, 263-273.

Mullis et al., "The Polymerase Chain Reaction: Why It Works", in Polymerase Chain Reaction, eds., Cold Spring Harbor Laboratory Press, Cold Spring Harbor, N.Y., 1989, 237-243.

Nelson et al., "Bifunctional oligonucleotide probes synthesized using a novel CPG support are able to detect single base pair mutations", Nucleic Acids Res. 17, 1989, 7187-7194.

Ng et al., "Frequent hypermethylation of p16 and p15 genes in multiple myeloma", Blood vol. 89, No. 7, 1997, 2500-6.

Ng et al., "MBD2 is a transcriptional repressor belonging to the MeCP1 histone deacetylase complex", Nature Genetics 23, 1999, 58-61.

Nowell et al., "The Clonal Evolution of Tumor Cell Populations", Science 194, 1976, 23-28.

Palmisano et al., "Predicting Lung Cancer by Detecting Aberrant Promoter Methylation in Sputum", Cancer Res. 50, 2000, 5954-5958.

Patel et al., "A single highly mutable catalytic site amino acid is critical for DNA polymerase fidelity", J Biol Chem vol. 276, No. 7, 2001, 5044-51.

Paz et al., "A systematic profile of DNA methylation in human cancer cell lines", Cancer Res 63, 2003, 1114-21.

Picketts et al., "Differential termination of primer extension: a novel, quantifiable method for detection of point mutations", Human Genetics 89, 1992, 155-157.

Radlowski et al., "Effect of disulfide and sulfhydryl reagents on abortive and productive elongation catalyzed by *Escherichia coli* RNA polymerase", Acta Biochim. Pol. vol. 41, No. No. 4, 1994, 415-419.

Rauch et al., "Methylated-CpG island recovery assay: a new technique for the rapid detection of methylated-CpG islands in cancer", Lab. Invest. 85, 2005, 1172-1180.

Rice et al., "Aberrant methylatton of the BRCAI CpG island promoter is associated with decreased BRCA1 mRNA in sporadic breast cancer cells", Oncogene 17, 1998, 1807-1812.

Robertson, "DNA methylation, methyltransferases, and cancer", Oncogene 20, 2001, 3139-3155.

Rosas et al., "Promoter hypermethylation patterns of p16, $O^6$-methylguanine-DNA-methyltransferase, and death-associated protein kinase in tumors and saliva of head and neck cancer patients", Cancer Res 61, 2001, 939-42.

Saiki et al., "Primer-Directed Enzymatic Amplification of DNA with a Thermostable DNA Polymerase", Science 239, 1988, 481-491.

Sakai et al., "Allele-specific hypermethylation of the retinoblastoma tumor-suppressor gene", Am J Hum Genet 48, 1991, 880-8.

Sanchez-Cespedes et al., "Gene promoter hypermethylation in tumors and serum of head and neck cancer patients.", Cancer Res 60, 2000, 892-5.

Sasaki et al., "Transcriptional sequencing: A method for DNA sequencing using RNA polymerase", Proc Natl Acad Sci USA 95, 1998, 3455-3460.

Sato et al., "Aberrant methylation of the HPP1 gene in ulcerative colitis-associated colorectal carcinoma", Cancer Res 62, 2002, 6820-2.

Sato et al., "Frequent hypomethylation of multiple genes overexpressed in pancreatic ductal adenocarcinoma", Cancer Res 63, 2003, 4158-66.

Shames et al., "A genome-wide screen for promoter methylation in lung cancer identifies novel methylation markers for multiple malignancies.", PLoS Med vol. 3, No. 2, 2006, e486, pp. 2244-2263.

Shen et al., "Optimizing annealing temperature overcomes bias in bisulfite PCR methylation analysis", Biotechniques vol. 42, No. 1, 2007, 48-58.

Shibata et al., "Hypermethylation of HPP1 is associated with hMLH1 hypermethylation in gastric adenocarcinomas", Cancer Res 62, 2002, 5637-40.

Singer-Sam et al., "A quantitative HpaII-PCR assay to measure methylation of DNA from a small number of cells", Nucleic Acids Res vol. 18, No. 3, 1990, 687.

Sinha et al., "Oligonucleotides with reporter groups attached to the 5'-terminus,", in Oligonucleotides and Analogues: A Practical Approach, Eckstein, F., ed., Oxford University Press, 1992, 185-189, 200-201.

Smithies et al., "Detection of Targeted Gene Modifications by Polymerase Chain Reaction", in Polymerase Chain Reaction, eds., Cold Spring Harbor Laboratory Press, Cold Spring Harbor, N.Y., 1989, 199-203.

Spangler et al., "TFIIH action in transcription initiation and promoter escap requires distinct regions of downstream promoter DNA", Proc. Natl. Acad. Set. USA vol. 98, No. 10, 2001, 5544-5549.

Sproat et al., "The synthesis of protected 5'-mercapto-2', 5'-dideoxyribonucleoside-3'-0-phosphoramidites; uses of 5'-mercapto-oligodeoxyribonucleotides", Nucleic Acids Res. vol. 15, No. 15, 1987, 4837-4848.

Tada et al., "MDR1 gene overexpression and altered degree of methylation at the promoter region in bladder cancer during chemotherapeutic treatment", Clin Cancer Res 6, 2000, 4618-27.

Tada et al., "The association of death-associated protein kinase hypermethylation with early recurrence in superficial bladder cancers", Cancer Res 62, 2002, 4048-53.

Takai et al., "Hypomethylation of LINE1 retrotransposon in human hepatocellular carcinomas, but not in surrounding liver cirrhosis.", Jpn J Clin Oncol 30, 2000, 306-9.

Tlsty et al., "Differences in the rates of gene amplification in nontumorigenic and tumorigenic cell lines as measured by Luria-Delbruck fluctuation analysis", Proc. Natl. Acad. Sci. USA 86, 1989, 9441-9445.

Toyota et al., "Aberrant methylation of the Cyclooxygenase 2 CpG island in colorectal tumors", Cancer Res 60, 2000, 4044-8.

Toyota et al., "The role of DNA hypermethylation in human neoplasia", Electrophoresis 21, 2000, 325-333.

Vaish et al., "Expanding the structural and functional diversity of RNA: analog uridine triphosphates as candidates for in vitro selection of nucleic acids", Nucl. Acids Res. 28, 2000, 3316-3322.

Veigl et al., "Biallelic inactivation of hMLH1 by epigenetic gene silencing, a novel mechanism causing human MSI cancers", Proc Natl Acad Sci U S A 95, 1998, 8698-702.

Vogelstein et al., "The multistep nature of cancer", Trends Genet. vol. 9, No. 4, 1993, 138-141.

Walker et al., "Isothermal in vitro amplification of DNA by a restriction enzyme/DNA polymerase system", Proc. Natl. Acad. Sci. USA 59, 1992, 392-396.

Wang et al., "Monovalent cations differ in their effects on transcription initiation from a σ-70 promoter of *Escherichia coli*", Gene 196, 1997, 95-98.

Warnecke et al., "Detection and measurement of PCR bias in quantitative methylation analysis of biculphite-treated DNA", Nucleic Acids Res 25:, 1997, 4422-6.

Weisenberger et al., "DNA methylation analysis by digital bisulfite genomic sequencing and digital MethyLight", Nucleic Acids Res vol. 36, No. 2008, 4689-98.

Wiencke et al., "Aberrant methylation of p16$^{INK4a}$ in anatomic and gender-specific subtypes of sporadic colorectal cancer", Cancer Epidemiol Biomarkers Prev 8, 1999, 501-6.

Wu et al., "The Ligation Amplification Reaction (LAR)—Amplification of Specific DNA Sequences Using Sequential Rounds of Template-Dependent Ligation", Genomics 4, 1989, 560-569.

Yegnasubramanian et al., "Combination of methylated-DNA precipitation and methylation-sensitive restriction enzymes (COMPARE-MS) for the rapid, sensitive and quantitative detection of DNA methylation", Nucleic Acids Res vol. 34, No. 3, 2006, e19, pp. 1-14.

Zeschnigk et al., "A novel real-time PCR assay for quantitative analysis of methylated alleles (QAMA): analysis of the retinoblastoma locus", Nucleic Acids Res 32, 2004, e125, pp. 1-5.

Zou et al., "Detection of aberrant p16 methylation in the serum of colorectal cancer patients", Clin Cancer Res 8, 2002, 188-91.

Zuckermann et al., "Efficient methods for attachment of thiol specific probes to the 3'-ends of synthetic oligodeoxyribonucleotides", Nucleic Acids Res vol. 15, No. 13, 1987, 5305-5321.

Zuker, "Mfold web server for nucleic acid folding and hybridization prediction", Nucleic Acids Res vol. 31, No. 13, 2003, 3406-15.

* cited by examiner

METHODS AND REAGENTS FOR DETECTING CPG METHYLATION WITH A METHYL CPG BINDING PROTEIN (MBP)

RELATED APPLICATIONS

This application claims the benefit of priority under 35 USC §119 of U.S. Provisional Application Ser. No. 61/053,648 filed May 15, 2008, the entire disclosure of which is incorporated herein by reference.

FIELD OF THE INVENTION

The present invention relates generally to the detection of methyl CpG in DNA. More specifically, the invention relates to detection of changes in methylation of DNA target sequences associated with disease.

BACKGROUND

Significance of CpG Methylation in Cancer

CpG islands are short genomic segments in the promoter regions of most human genes that are enriched in the dinucleotide CpG. CpG islands are unmethylated in normal tissues but become progressively more methylated in cancer cells, leading to repression of genes that control the cell cycle.

Cancer is actively avoided through the expression of numerous tumor-suppressor genes that regulate the cell division cycle and mediate interactions among cells. Studies of benign and malignant tumors have shown that cancer develops in a multi-step process where randomly accumulated changes either enhance the expression of proto-oncogenes or reduce the expression or function of tumor-suppressor and DNA repair genes (Nowell et al. (1976) Science 194:23-28). Somatic mutations account for some of these changes in tumor-suppressor and DNA repair genes. However, it has recently become apparent that epigenetic changes such as DNA hypermethylation and hypomethylation also play a large role in the development of cancer through inactivation of tumor suppressors or enhancement of proto-oncogenes (Esteller (2007) Nat. Rev. Genet. 8:286-98; Feinberg & Vogelstein (1983) Nature 301:89-92; Paluszczak & Baer-Dubowska (2006) J. Appl. Genet. 47:365-75; Vogelstein & Kinzler (1993) Trends Genet. 9:138-41). Virtually all systems for avoiding transformation can be disabled by epigenetic inactivation via hypermethylation (Esteller et al. (2001) Cancer Res. 61:3225-29). These changes occur at discrete clusters of CpG sites but in the context of a global reduction in cytosine methylation (Feinberg & Vogelstein (1983) Nature 301:89-92; Gama-Sosa et al. (1983) 11:6883-94). The pathways for detecting and dealing with DNA damage/replication errors can also be disabled by methylation changes, allowing additional mutations to accumulate and cause genomic instability. The expression of key genes can be altered either by an increase (hypermethylation) or a decrease (hypomethylation) of methylation at promoter CpG islands. Hypermethylation at promoter CpG islands of tumor suppressor genes results in a decrease in their expression level.

Hypermethylation of CpG promoter islands occurs at an early stage of cancer development and is found in virtually all tumors, making it potentially very useful as a diagnostic marker (reviewed in Esteller (2007) Nat. Rev. Genet. 8:286-98; Paluszczak & Baer-Dubowska (2006) J. Appl. Genet. 47:365-75), allowing cancer to be noninvasively detected in the early stages when treatment is most effective. Hypermethylation of the promoter region of genes such as DAP kinase, p16, and MGMT can be detected in the sputum of smokers up to 3 years prior to the diagnosis of squamous cell lung carcinoma (Belinsky et al. (2006) Cancer Res. 66:3338-44; Palmisano et al. (2000) Cancer Res. 60:5954-58). Similarly, hypermethylation of a small panel of genes may be a valuable early detection method for non-small cell lung cancer (Kim et al. (2004) J. Clin. Oncol. 22:2363-70). Hypermethylation of a small panel of genes was detected in the early stages of breast cancer from nipple aspirate fluid but was not detected in normal or benign breast tissue (Krassenstein et al. (2004) Clin. Cancer. Res. 10:28-32). Hypermethylation of GSTP1 is found in >90% of prostate cancers, can be detected via analysis of urine, and is not found in normal tissue or benign prostate lesions (Cairns et al. (2001) Clin. Cancer Res. 7:2727-30; Henrique & Jeronimo (2004) Eur. Urol. 46:660-69: 16 Jeronimo et al. (2004) Clin. Cancer Res. 10:8472-78). Hypermethylation of DAP kinase and p16 are found in premalignant cells in bladder cancer and the early stages of gastric carcinoma (Kang et al. (2001) Cancer Res. 61:2847-51; Tada et al. (2002) Cancer Res. 62:4048-53). A recent genome-wide screen of promoter methylation patterns in various cancers suggested that primary lung, breast, colon, and prostate cancers may share a promoter hypermethylation signature that can be used for early detection screening (Shames et al. (2006) PLoS Med. 3:e486).

In addition to acting as markers for early cancer detection, hypermethylation of promoter CpG islands may act as markers of tumor prognosis and potential for relapse. Hypermethylation of E-cadherin is associated with shorter disease-free survival in gastric and tongue cancer (Chang et al. (2002) Cancer 94:386-92; Graziano et al. (2004) Clin. Cancer Res. 10:2784-89). Hypermethylation of DAP kinase, p16, and EMP3 are linked to tumor aggressiveness in lung, colorectal, and brain cancer (Esteller (2005) Ann. Rev. Pharmacol. Toxicol. 45:629-56). Hypermethylation of calcitonin in lymphoblastic leukemia is associated with an increased risk of relapse. DNA hypermethylation profiles could potentially be used to determine cancer subtype, which can help determine risk and prognosis. One recent study found a clustering of neuroblastomas according to risk based on the methylation profile of a panel of genes (Alaminos et al. (2004) J.N.C.I. 96:1208-19). Another recent study found that subtypes of renal cancer could be distinguished based on multiple gene methylation profiles (Gonzalgo et al. (2004) Clin. Cancer Res. 10:7276-83). Finally, methylation profiling has been used to determine a multifocal versus metastatic origin for multiple hepatocellular carcinomas, which may lead to differential treatment and prognosis (Anzola et al. (2004) Scand. J. Gastroenterol. 39:246-51).

Hypermethylation events can also be used as a predictor of chemotherapy response and as a tool for monitoring the success of chemotherapy and potential for relapse. Knowledge of the methylation level of certain genes in primary tumors may indicate tumor response to various chemotherapeutic agents, allowing therapy to be tailored to the individual. This would increase the efficiency of treatment and spare patients unnecessary side effects of drugs with a low probability of shrinking tumor size. Hypermethylation of DNA repair genes can confer chemosensitivity, while hypermethylation of proapoptotic genes can confer chemotherapy resistance (Esteller (2000) Eur. J. Cancer 36:2294-2300; Soengas et al. (2001) Nature 409:207-11). Methylation of ATM correlates with increased radiosensitivity of colorectal tumor cells (Kim et al. (2002) Oncogene 21:3864-71). Sensitivity of gastric cancers to microtubule inhibitors depends on the hypermethylation state of CHFR (Satoh et al. (2003) Cancer Res. 63:8606-13). MGMT hypermethylation can predict the response of gliomas to the chemotherapeutic drugs BCNU and temozolomide, of melanomas to fotemustine, and of tumors to cyclophosphamide (Esteller (2000) Eur. J. Cancer 36:2294-2300; Christmann et al. (2001) Int. J. Cancer 92:123-29; Esteller et al. (2002) J. Natl. Cancer Inst. 94:26-32; Hegi et al. (2005) N. Engl. J. Med. 352:997-1003). Hypermethylation of COX2 can reduce the effectiveness of COX2 inhibitors (Toyota et al. (2000) Cancer Res. 60:4044-48). The hypermethylation states of phosphoserine aminotransferase or ESR1 are the best predictors of breast cancer response to tamoxifen therapy (Martens et al. (2005) Cancer Res. 65:4101-17. Widschwendter et al. (2004) Cancer Res. 64:3807-13), and the hypermethylation state of RASSF1A can be used to monitor the efficiency of the therapy (Fiegl et al. (2005) Cancer Res. 65:1141-45). Finally, hypermethylation of a panel of genes can be used to detect and monitor residual disease or relapse in natural killer cell lymphoma, and has a higher sensitivity than histological tests (Siu et al. (2003) Br. J. Haematol. 122:70-77).

Methods for Detecting Methylated-CpGs

A number of methods have been used to detect methylated-CpG (mCpG) in target DNA. The three primary methods in current use are detailed below.

Bisulfite Methods. The most commonly used methylation detection methods utilize bisulfite modification of DNA, resulting in deamination of cytosine residues to uracil while leaving the methylated cytosines unchanged. Upon PCR amplification, the methylated cytosine is copied to cytosine and uracil is copied to thymine. As a result, the retention of cytosine at a specific position indicates methylation. The modified DNA can then be analyzed by sequence analysis, methylation-specific PCR (MSP) (Herman et al. (1996) Proc. Natl. Acad. Sci. USA 93:9821-26), hybridization (e.g. to a microarray or blot) and the like. In MSP, a pair of methylation-specific oligonucleotide primers is added to the bisulfite-treated DNA and PCR is performed in order to amplify the target DNA. Fluorescence-based quantitative real-time PCR can also be performed on bisulfite-modified DNA (Eads et al. (2000) Nucl. Acids Res. 28:E32; Zeschnigk et al. (2004) Nucl. Acids Res. 32:e125).

Commercial kits, reagents and systems employing bisulfite treatment for analyzing mCpG are available. Epigenomics (Berlin) has two variants of the MethylLight assay, adaptations of quantitative real-time PCR, called Quantitative MethylLight (QM) and Heavy Methyl (HM). QM utilizes Taqman® probes to generate the fluorescent signal. During the course of amplification, the fluor is cleaved from the Taqman® probe resulting in fluorescence that can be detected in real-time (Wojdacz & Dobrovic (2007) Nucl. Acids Res. 35:e41). HM is an adaptation of QM in which blocker oligonucleotides are added to the reaction. These blocker oligonucleotides prevent the amplification from unmethylated DNA, resulting in increased assay sensitivity (Cottrell et al. (2004) Nucl. Acids Res. 32:e10). Pyrosequencing® is also utilized for methylation quantitation from bisulfite-modified DNA, as exemplified by the Pyro Q-CpG™ system from Biotage (Uppsala, Sweden; Tost et al. (2003) Biotechniques 35:152-56).

Although bisulfite modification is a widely used and an established procedure for detecting CpG methylation, bisulfite treatment can destroy a large percentage of the input DNA, resulting in limited sensitivity and requiring large quantities of sample DNA. Extensive degradation can introduce sampling errors when few molecules are long enough to be amplified (Ehrich et al. (2007) Nucl. Acids Res. 35:e29). Furthermore, the assays are time-consuming, require a harsh base denaturation step, and have a high-probability of false-positive results due to the incomplete cytosine deamination during bisulfite treatment.

Methylation-Sensitive Restriction Enzyme Digestion Methods. A second method for detection of mCpG in DNA relies on restriction enzyme analysis. DNA is treated with either a MSRE (methylation-sensitive restriction enzyme) or a MDRE (methylation dependent restriction enzyme), amplified and then analyzed by microarray or gel electrophoresis. MSREs such as HpaII and AciI cut a sequence only if it is unmethylated. MDREs are restriction enzymes that require methylation of a DNA sequence for cleavage. By treating a sample of DNA with either of these enzymes and subsequent comparison to a control sample, the methylation state of a DNA sample can be determined. If digestion of a specific DNA sample occurs after treatment with a MDRE, then the DNA is assumed to be methylated. Conversely, if the DNA is uncut when treated with a MSRE, then this sample is also assumed to be methylated. By comparing the amount of cut vs. uncut DNA, the level of methylation can be estimated. A common read-out for this type of methylation analysis is the subsequent amplification and fluorescent labeling of the digested DNA. The fragments can then by hybridized to a library microarray and analyzed or simply resolved by electrophoresis.

Commercially available systems include Orion's MethylScope®, a system that utilizes restriction enzymes and a microarray read-out (Lippman et al. (2004) Nature 430:471-76), and MethyScreen, which employs quantitative real-time PCR (Ordway et al. (2006) Carcinogenesis 27:2409-23).

An advantage of MSRE/MDRE digestion is that no pre-treatment of the DNA is necessary, although it is often performed in conjunction with bisulfite treatment of DNA in a procedure called COBRA (Xiong & Laird (1997) Nucl. Acids Res. 25:2532-34). Some disadvantages with this application are that it is a rather lengthy procedure and is dependent on the presence of recognition sequences. Furthermore, this approach is relatively inefficient, which can reduce the reliability of the results.

Chromatin Immunoprecitipation Methods. A third method that is commonly employed for detecting mCpG is chromatin immunoprecipitation (ChIP). Typically, cells are fixed, and then methylated DNA is immunoprecipitated by the use of antibodies specific for methyl binding proteins. The resulting DNA is amplified, labeled and analyzed by hybridization in a microarray assay. The advantages of this method are that the assay can be performed from live cells with little or no DNA purification required. The assay also has increased sensitivity, as unwanted and contaminant DNA are removed prior to analysis. However, the procedure is very time-consuming, involves several steps and requires expensive reagents. Some assays may take as long as five days to complete.

Given the importance of CpG methylation in cancer development and progression, a rapid, reliable, and sensitive test for methylated CpG DNA would provide an important and useful tool for cancer detection, diagnosis and monitoring.

SUMMARY OF THE INVENTION

The present invention provides fusion polypeptides that bind to methyl CpG. Such fusion polypeptides include a methyl-CpG binding domain (MBD) and an affinity tag, wherein the fusion polypeptide binds. In certain aspects of the invention the MBD is a MBD2 methyl binding domain or a MeCP2 methyl binding domain.

The fusion polypeptides of the invention can be constructed to include convenient sites for conjugation to other molecular species. For example, in certain embodiments of the invention, the fusion polypeptide includes at least one reactive cysteine residue in a position that is not essential for binding of the fusion polypeptide to methylated DNA.

The affinity tag of the fusion polypeptide provides a convenient means for isolating the polypeptide and can be any affinity tag known in the art. A Particularly useful affinity tag that can be included in the fusion polypeptides of the invention is a glutathione-S-transferase (GST) domain.

Also provided are polynucleotides encoding the fusion polypeptides of the invention. Conveniently, the polynucleotides can be designed to contain one or more one codons has been optimized for polypeptide expression in a bacterial cell.

The present invention also provides mCpG detectors that include a methyl binding polypeptide linked to at least one abortive promoter cassette (APC). In certain embodiments, the mCpG detector includes a methyl CpG binding fusion polypeptide such as a fusion polypeptide containing a MBD (e.g. MBD2 or MeCP2), linked to at least one APC.

The APC of the mCpG detectors according to the invention can be covalently linked to an amino acid of the methyl binding polypeptide. Alternatively, the APC can be indirectly linked to the methyl binding polypeptide, such as through an antibody that binds to the methyl binding polypeptide. In one embodiment of the invention, the mCpG detector is methyl binding fusion polypeptide that includes a MBD and an affinity tag. Thus, in these embodiments, an APC can be indirectly linked to the mCpG detector through an antibody to the affinity tag.

The present invention also provides methods for detecting a CpG methylated DNA fragment that includes the steps of
a) contacting the methylated DNA fragment with a mCpG detector of the invention, such that the mCpG detector binds to at least one mCpG on the methylated DNA fragment, and thereby forms a detector-mCpG complex;
b) incubating the detector-mCpG complex with a solution comprising RNA polymerase, a transcription initiator and a transcription terminator, to synthesize Abscripts from a promoter in the APC; and
c) detecting the Abscripts synthesized in step b), such as by mass spectrometry or TLC, thereby detecting the methylated DNA.

The Abscripts are typically short oligonucleotides. In certain embodiment, the Abscripts are trinucleotides. In certain embodiments of these methods method, the transcription initiator is a dinucleotide. In certain aspects, the transcription terminator is an O-methyl nucleoside triphosphate.

In another embodiment, the invention provides a method for detecting a CpG methylated DNA fragment that includes the steps of:
a) capturing a CpG methylated DNA fragment on a solid support;
b) contacting the captured methylated DNA fragment with a mCpG detector of the invention, such that the detector binds to at least one mCpG on the CpG methylated DNA fragment, thereby forming a captured complex;
c) incubating the captured complex with a solution comprising RNA polymerase, a transcription initiator and a transcription terminator to synthesize Abscripts from a promoter in the APC; and
d) detecting the Abscripts synthesized in step b), thereby detecting the CpG methylated DNA fragment.

The CpG methylated DNA fragment can, for example be a restriction fragment of genomic DNA from a clinical specimen of a subject, such as a blood, sputum, saliva, urine, semen, stool, bodily discharge, exudate, aspirate or tissue sample. In certain aspects of the invention, the subject may be suspected of having cancer. The method will be particularly useful where the CpG methylated DNA fragment is normally unmethylated (ie. is not methylated in normal cells or tissues), but is methylated in cancer. In such cases a correlation between the detecting the CpG methylated DNA and the presence of cancer in the subject can be made.

Capture of the CpG methylated DNA fragment on the solid support can be accomplished by: denaturing the CpG methylated DNA fragment; hybridizing the denatured CpG methylated DNA fragment to a biotinylated capture probe that is complementary to a nucleotide sequence of the CpG methylated DNA to form a biotin-CpG methylated DNA complex; contacting the biotin-CpG methylated DNA complex with a streptavidin coated solid support to immobilize the CpG methylated DNA; hybridizing the immobilized CpG methylated DNA with a mCpG probe that forms a duplex with at least one mCpG of the immobilized CpG methylated DNA; and removing unbound CpG methylated DNA and mCpG probe from the solid support. In certain aspects, the mCpG probe is complementary to a CpG island. The method may be used, for example, where the cytosine of each CpG of the mCpG probe is methylated.

In yet another embodiment, the invention provides methods for detecting a CpG methylated DNA fragment that include the steps of
a) annealing a biotinylated capture probe to a denatured, CpG methylated DNA fragment to form a partially duplex methylated DNA fragment;
b) contacting the partially duplex methylated DNA fragment with streptavidin-coated magnetic beads to capture the CpG methylated DNA fragment;
c) hybridizing the captured CpG methylated DNA with a mCpG probe such that the probe forms a duplex with at least one mCpG of the captured CpG methylated DNA fragment;
d) contacting the captured methylated DNA fragment with a mCpG detector of the invention such that the detector binds to at least one duplex mCpG on the CpG methylated DNA fragment;
e) incubating the CpG methylated DNA-bound detector of step d) with a solution comprising RNA polymerase, a transcription initiator and a transcription terminator, such that Abscripts are synthesized from a promoter in the APC; and
f) detecting the Abscripts synthesized in step e).

In yet a further embodiment of the invention, methods for detecting cancer in a subject are provided. Such method include detecting a CpG methylated DNA fragment in a sample from the subject according to the methods set forth above, where the CpG methylated DNA fragment is normally unmethylated, but is methylated in cancer. Thus, detection of a CpG methylated DNA, methylated by this method of the invention is indicative of cancer in the subject. In certain aspects, the such CpG methylated DNA includes a CpG island sequence. The cancer can be, for example, lung cancer, breast cancer, colorectal cancer, prostate cancer, bladder cancer, gastric cancer, brain cancer, renal cancer, liver cancer, leukemia, or any cancer where CpG methylation is correlated to cancer.

Also provided by the invention are kits for detecting CpG methylation that include a container containing a mCpG detector of the invention and instructions for detecting CpG methylation using the detector. The kit may also include an RNA polymerase, an initiator, a terminator, a capture probe and/or a mCpG probe. Kits for preparing a mCpG detector are also encompassed by the present invention and may include a container containing a mCpG TSP, at least one APC, and instructions for conjugating the APC to the mCpG TSP. In certain embodiments, multiple APC are included in the kit.

For example, the kit may include 2 to about 20 different APCs for multiplex CpG methylation detection.

In yet another embodiment, the invention provides arrays that include 1 to about 1000 CpG island capture probes immobilized on a solid support, where each CpG island capture probe hybridizes to a nucleotide sequence adjacent to a CpG island.

DETAILED DESCRIPTION

Figure 1:
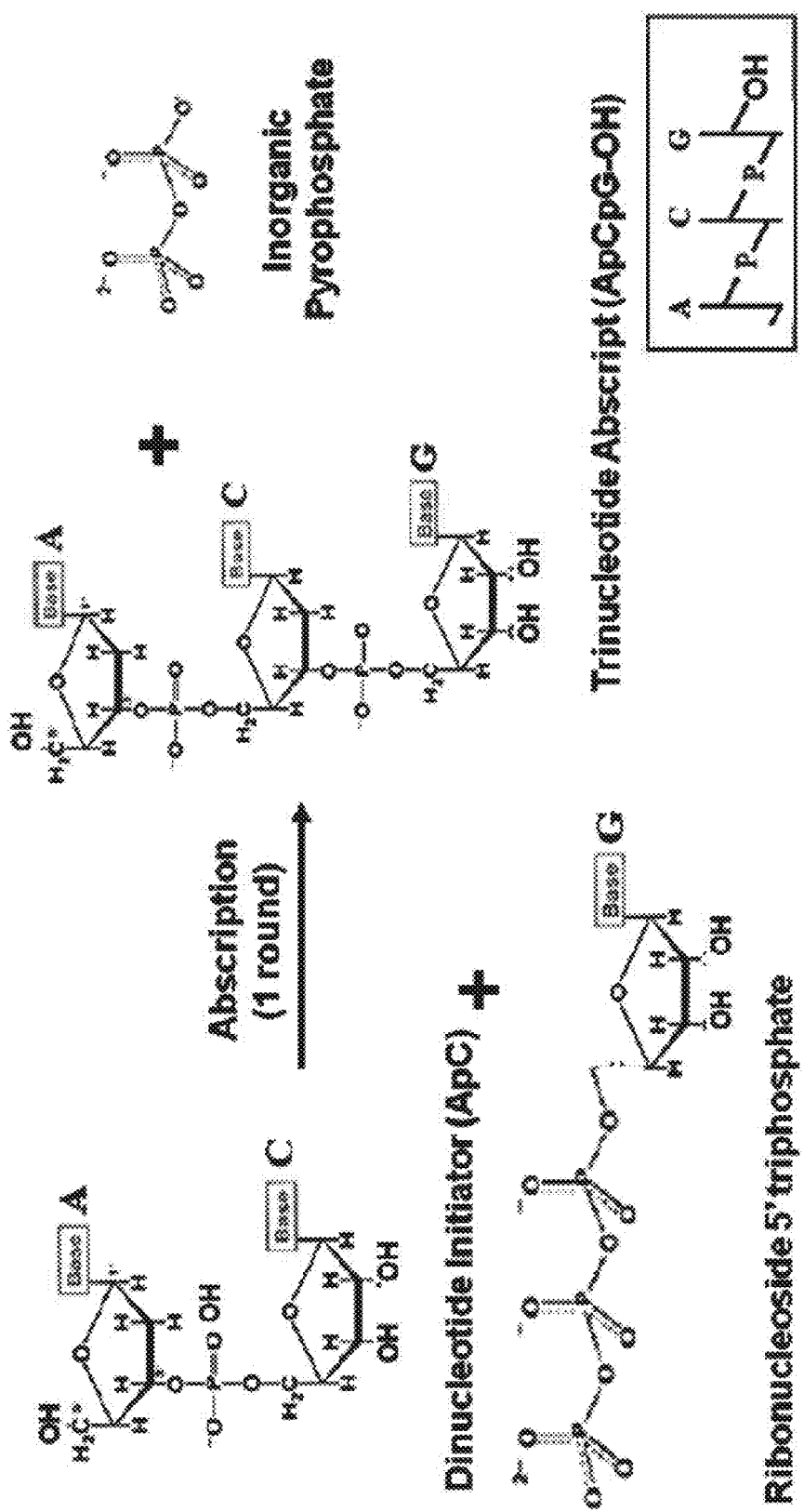
FIG. 1 Illustrates the production of an exemplary trinucleotide Abscript from a dinucleotide initiator and GTP.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. As used herein, the terms "comprises," "comprising", "includes", and "including", or any other variations thereof, are intended to cover a non-exclusive inclusion, such that a process, method, composition, reaction mixture, kit, or apparatus that comprises a list of elements does not include only those elements but may include other elements not expressly listed or inherent to such process, method, composition, reaction mixture, kit, or apparatus. The section headings used herein are for organizational purposes only and are not to be construed as limiting the subject matter described.

Definitions

Unless specific definitions are provided, the nomenclatures utilized in connection with, and the laboratory procedures and techniques of molecular biology, biochemistry, and organic chemistry described herein are those known in the art. Standard chemical and biological symbols and abbreviations are used interchangeably with the full names represented by such symbols and abbreviations. Thus, for example, the terms "deoxyribonucleic acid" and "DNA" are understood to have identical meaning. Standard techniques may be used e.g., for chemical syntheses, chemical analyses, recombinant DNA methodology, and oligonucleotide synthesis. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)); Ausubel et al., *Current Protocols in Molecular Biology* (John Wiley & Sons Inc., N.Y. (2003)), the contents of which are incorporated by reference herein in their entirety for any purpose.

"About" as used herein means that a number referred to as "about" comprises the recited number plus or minus 1-10% of that recited number. For example, "about" 50 nucleotides can mean 45-55 nucleotides or as few as 49-51 nucleotides depending on the situation. Whenever it appears herein, a numerical range, such as "45-55", refers to each integer in the given range; e.g., "45-55 nucleotides" means that the nucleic acid can contain 45 nucleotides, 46 nucleotides, etc., up to and including 55 nucleotides.

"Transcription" as used herein, refers to the enzymatic synthesis of an RNA copy of one strand of DNA (i.e, template) catalyzed by an RNA polymerase (e.g. a DNA-dependent RNA polymerase).

"Abortive transcription" is an RNA polymerase-mediated process that reiteratively synthesizes and terminates the synthesis of oligonucleotides that correspond to at least one portion of a complementary nucleic acid template sequence. Abortive oligonucleotides synthesized in vivo vary in length of nucleotides, and are complementary to a sequence at or near the transcription initiation site.

"Abscription" is a form of abortive transcription optimized for in vitro analytical use to reiteratively produce short, uniform RNA transcripts or "Abscripts" from a synthetic promoter at high frequency.

"Reiterative" refers to the repetitive synthesis of multiple identical or substantially identical copies of a sequence of interest. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

"Terminator" or "transcription terminator" as used herein, refers to an RNA chain terminating compound, complex or process. A terminator of the invention can, for example, be a nucleotide analog, which can be incorporated into an RNA chain during RNA synthesis to prevent the addition of additional nucleotides to the RNA chain.

A "target DNA sequence" is a DNA sequence of interest for which detection, characterization or quantification is desired. The actual nucleotide sequence of the target sequence may be known or not known. Target DNAs are typically DNAs for which the CpG methylation status is interrogated. A "target DNA fragment" is a segment of DNA containing the target DNA sequence. Target DNA fragments can be produced by any method including e.g., shearing or sonication, but most typically are generated by digestion with one or more restriction endonucleases.

As used herein, a "template" is a polynucleotide from which a complementary oligo- or polynucleotide copy is synthesized.

"Synthesis" generally refers to the process of producing a nucleic acid, via chemical or enzymatic means. More typically, chemical synthesis is used for single strands of a nucleic acid. Enzyme mediated "Synthesis" encompasses both transcription and replication from a template. Synthesis includes a single copy or multiple copies of the target. "Multiple copies" means at least 2 copies. A "copy" does not necessarily mean perfect sequence complementarity or identity with the template sequence. For example, copies can include nucleotide analogs, intentional sequence alterations (such as sequence alterations introduced through a primer comprising a sequence that is hybridizable, but not complementary, to the template), and/or sequence errors that occur during synthesis.

The terms "polynucleotide" and "nucleic acid (molecule)" are used interchangeably to refer to polymeric forms of nucleotides of any length. The polynucleotides may contain deoxyribonucleotides, ribonucleotides and/or their analogs. Nucleotides may be modified or unmodified and have any three-dimensional structure, and may perform any function, known or unknown. The term "polynucleotide" includes single-, double-stranded and triple helical molecules. The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers.

"Oligonucleotide" refers to polynucleotides of between 2 and about 100 nucleotides of single- or double-stranded nucleic acid, typically DNA or RNA. Oligonucleotides are also known as oligomers or oligos and may be isolated from genes, or chemically synthesized by methods known in the art. A "primer" refers to an oligonucleotide containing at least 6 nucleotides, usually single-stranded, that provides a 3'-hydroxyl end for the initiation of enzyme-mediated nucleic acid synthesis. A "polynucleotide probe" is a polynucleotide that specifically hybridizes to a complementary polynucleotide sequence.

"Nucleic acid sequence" refers to the sequence of nucleotide bases in an oligonucleotide or polynucleotide, such as DNA or RNA. For double strand molecules, a single strand may be used to represent both strands, the complementary stand being inferred by Watson-Crick base pairing.

The terms "complementary" or "complementarity" are used in reference to a first polynucleotide (which may be an oligonucleotide) which is in "antiparallel association" with a second polynucleotide (which also may be an oligonucleotide). As used herein, the term "antiparallel association" refers to the alignment of two polynucleotides such that individual nucleotides or bases of the two associated polynucleotides are paired substantially in accordance with Watson-Crick base-pairing rules. Complementarity may be "partial," in which only some of the polynucleotides' bases are matched according to the base pairing rules. Or, there may be "complete" or "total" complementarity between the polynucleotides. Those skilled in the art of nucleic acid technology can determine duplex stability empirically by considering a number of variables, including, for example, the length of the first polynucleotide, which may be an oligonucleotide, the base composition and sequence of the first polynucleotide, and the ionic strength and incidence of mismatched base pairs.

As used herein, the term "hybridization" is used in reference to the base-pairing of complementary nucleic acids, including polynucleotides and oligonucleotides containing 6 or more nucleotides. Hybridization and the strength of hybridization (i.e., the strength of the association between the nucleic acids) is impacted by such factors as the degree of complementary between the nucleic acids, the stringency of the reaction conditions involved, the melting temperature ($T_m$) of the formed hybrid, and the G:C ratio within the duplex nucleic acid. Generally, "hybridization" methods involve annealing a complementary polynucleotide to a target nucleic acid (i.e., the sequence to be detected either by direct or indirect means). The ability of two polynucleotides and/or oligonucleotides containing complementary sequences to locate each other and anneal to one another through base pairing interactions is a well-recognized phenomenon.

A "complex" is an assembly of components. A complex may or may not be stable and may be directly or indirectly detected. For example, as described herein, given certain components of a reaction and the type of product(s) of the reaction, the existence of a complex can be inferred. For example, in the abortive transcription method described herein, a complex is generally an intermediate with respect to a final reiterative synthesis product, such as a final abortive transcription or replication product.

A "detector" as used herein, refers to a molecule or complex that can be used to detect another molecule (e.g. a target). Detectors of the present invention typically include a target specific probe linked directly or indirectly to an abortive promoter cassette. More particularly, mCpG detectors of the invention include a methyl CpG binding TSP, such as a methyl-CpG binding domain.

"Methylation" refers to the addition of a methyl group ($—CH_3$) to a nucleotide base in DNA or RNA.

"Microarray" and "array," are used interchangeably to refer to an arrangement of a collection compounds, samples, or molecules such as oligo- or polynucleotides. Arrays are typically "addressable" such that individual members of the collection have a unique, identifiable position within the arrangement. Arrays can be on a solid substrate, such as a glass slide, or on a semi-solid substrate, such as nitrocellulose membrane, or in vessels, such as tubes or microtiter plate wells. A typical arrangement for an array is an 8 row by 12 column configuration, such as with a microtiter plate.

The term "solid support" refers to any solid phase that can be used to immobilize e.g., a capture probe or other oligo- or polynucleotide, a polypeptide, an antibody or other desired molecule or complex. Suitable solid supports will be well known in the art and include, but are not limited to, the walls of wells of a reaction tray, such as a microtiter plate, the walls of test tubes, polystyrene beads, paramagnetic or non-magnetic beads, glass slides, nitrocellulose membranes, nylon membranes, and microparticles such as latex particles. Typical materials for solid supports include, but are not limited to, polyvinyl chloride (PVC), polystytrene, cellulose, nylon, latex and derivatives thereof. Further, the solid support may be coated, derivatized or otherwise modified to promote adhesion of the desired molecules and/or to deter non-specific binding or other undesired interactions. The choice of a specific "solid phase" is usually not critical and can be selected by one skilled in the art depending on the assay employed. Conveniently, the solid support can be selected to accommodate various detection methods. For example, 96 or 384 well plates can be used for assays that will be automated, for example by robotic workstations, and/or those that will be detected using, for example, a plate reader. For methods of the present invention that may involve e.g. an autoradiographic detection step utilizing a film-based visualization, the solid support may be a thin membrane, such as a nitrocellulose or nylon membrane, a gel or a thin layer chromatography plate. Suitable methods for immobilizing molecules on solid phases include ionic, hydrophobic, covalent interactions and the like, and combinations thereof. However, the method of immobilization is not typically important, and may involve uncharacterized adsorption mechanisms. A "solid support" as used herein, may thus refer to any material which is insoluble, or can be made insoluble by a subsequent reaction. The solid support can be chosen for its intrinsic ability to attract and immobilize a capture reagent. Alternatively, the solid support can retain additional molecules which have the ability to attract and immobilize e.g., a capture reagent.

"Antibody" or "antibodies", as used herein, include naturally occurring species such as polyclonal and monoclonal antibodies as well as any antigen-binding portion, fragment or subunit of a naturally occurring molecule, such as for example Fab, Fab', and F(ab)$_2$ fragments of an antibody. Also contemplated for use in the methods of the invention are recombinant, truncated, single chain, chimeric, and hybrid antibodies, including, but not limited to, humanized and primatized antibodies, and other non-naturally occurring antibody forms.

The present invention provides a simple and sensitive technology for the detection of CpG methylation in DNA via mCpG target site probes that include optimized methyl binding domain (MBD) polypeptides. The mCpG target site probes are coupled directly or indirectly to a signal generator, which produces a detectable signal that can be measured as an indicator of CpG methylation.

In certain embodiments of the invention, signal generation is based on an Abscription (Abortive Transcription) process in which DNA signal generators called Abortive Promoter Cassettes (APCs) are bound to target mCpG sites via the mCpG target specific probes. RNA polymerase produces uniform, short RNA molecules from synthetic or natural abortive promoters in APCs as signals of the presence of methylated CpGs. In other embodiments of the invention, signal generating cassettes can produce detectable RNA or DNA signals through PCR or other replication and/or amplification methods.

In further embodiments of the invention, signal generation can be based on enzyme-coupled systems, such as horseradish peroxidase (HRP), alkaline phosphatase (AP), or β-galactosidase (β-gal). Such systems are typically coupled to mCpG target specific probes through direct or indirect association with the MBD polypeptides. For example, the enzyme can be covalently attached to the MBD polypeptide, bound to the MBD polypeptide through an antibody, or associated through an affinity binding pair (e.g. biotin-streptavidin).

The methods of the invention offer significant advantages over current CpG methylation detection methods. Although the methods described herein can be adapted for detecting methylation in bisulfite-treated DNA (as detailed in Example 12, below), bisulfite treatment is not required. Thus, the extensive DNA degradation and the reduction of sequence complexity associated with chemical treatment of target DNA can be avoided entirely in certain embodiments of the invention. The methods of the invention are rapid and can typically be performed in a single day. Furthermore, the invention can be adapted to multiplex and automated applications.

Abscription Technology

Abscription technology is based on the observation that prior to the initiation of full-length RNA transcription, a large number of short, abortive transcripts are synthesized by RNA polymerases before full-length RNA transcripts are made. As described below, abortive transcripts are a normal by-product of the transcription process, yet are distinguishable from full-length RNA transcripts (which are the functionally informative product of the transcription process), in both size and in the manner in which they are made.

Transcription Process. Transcription is a complex and highly regulated process utilized by both eukaryotes and prokaryotes to selectively synthesize RNA transcripts from DNA templates (i.e. genes) (reviewed in Record et al. (1996) *Escherichia coli and Salmonella*, (Neidhart, ed.; ASM Press, Washington, D.C.); deHaseth et al. (1998) J. Bact. 180:3019-25; Hsu (2002) Biochim. Biophys. Acta. 1577:191-207; Murakami & Darst (2003) Curr. Opin. Struct. Biol. 13:31-39; Young et al. (2002). Cell. 109:417-420). Transcription in a cellular environment includes 5 stages: 1. Preinitiation, during which transcriptional machinery (e.g. RNA polymerase (RNAP) and transcription factors), is recruited to a promoter; 2. Initiation, during which synthesis of RNA begins; 3. Promoter Escape, during which the RNA polymerase leaves the promoter and abortive initiation stops (usually after synthesis of approximately 12-mer RNAs); 4. Elongation, during which RNAP travels processively along the template DNA strand, thereby synthesizing a full-length RNA transcript; and 5. Termination, during which RNA synthesis ceases and RNAP dissociates from the template DNA.

Production of Abortive Transcripts Prior to Full-Length RNA Transcription. Typically, RNAP fails to escape from the promoter on its first attempt and, instead, engages in multiple abortive cycles of synthesis and release of short RNA products called abortive transcripts. Only when RNAP succeeds in synthesizing an RNA product of a threshold length does RNAP irrevocably break its interactions with promoter DNA, and begin to translocate along the DNA template, processively synthesizing a full-length RNA transcript (see Hsu (2002) Biochim. Biophys. Acta. 1577:191-207; Hsu et al. (2003) Biochemistry 42: 3777-86; Vo et al. (2003) Biochemistry 42:3787-97; Vo et al. (2003) Biochemistry: 42:3798-11). Prior to promoter escape in (phase 3, above), RNAP remains bound to template DNA at or near the promoter region, thereby allowing multiple rounds of abortive synthesis in a short time.

Abscription Technology. Abscription technology exploits the natural phenomenon of abortive RNA synthesis to produce large numbers of detectable abortive transcripts (Abscripts). Abscription is an isothermal, robust, linear signal generation system based on Abortive Transcription. In an Abscription method, Abortive Promoter Cassettes (APCs) are bound to target molecules via Target Site Probes (TSPs). An RNA polymerase, such as $E.\ coli$ RNA polymerase, then uses the APC as a template for generating large numbers of signals per target in the form of short, uniform RNA molecules or Abscripts (abortive transcripts).

Abscription detection methods have three basic steps that can be adapted to detect a wide variety of molecules of interest. First, an APC is localized to a target molecule of interest through a Target Site Probe (TSP). Second, Abscripts are synthesized from the localized APCs. Finally, Abscripts are detected as a means of target detection and may be quantified to assess the amount of a target present. The process is very efficient because the RNAP does not move away or dissociate from the promoter between rounds of abortive RNA synthesis, as it does after producing each full-length transcript. Furthermore, only uniform, short RNA signals are synthesized, which can be produced more quickly and with less effort than longer oligo- and polynucleotides.

Although the factors and conditions required for promoter escape (and hence the end of abortive synthesis), are incompletely understood, sufficient knowledge is available to create a synthetic environment that favors abortive transcript synthesis and precludes full-length RNA production. In one embodiment, Abscription is controlled at the synthesis stage to produce Abscripts that are initiated with a defined dinucleotide initiator and then terminated after the addition of one or more NTPs as illustrated in the nonlimiting example shown in FIG. 1. Abscript length can be limited to as short as 3 nucleotides (nt) with the use of chain terminating NTPs (e.g., 3'-O-Me-NTPs) or by omitting one or more NTPs from the reaction.

In other embodiments, Abscript length is controlled at the promoter/template stage, by providing synthetic templates that have a discrete, limited number of nucleotides available for transcription before a stop signal is reached. The uniformity of Abscript production from a single APC in a single Abscription reaction means that Abscript signals are directly proportional to the amount of target present. Thus Abscription is both a qualitative and quantitative system for measuring a target, such as mCpG.

Target Site Probes. APCs can be coupled to wide variety of TSPs, including but not limited to oligonucleotides, polynucleotides, antibodies, ligands and other target binding species, such as mCpG binding proteins. TSPs provide specificity in Abscription methods by directing APCs to the target of interest. Abscription thus provides a robust, isothermal method for detecting and quantifying a wide range of targets.

Abortive Promoter Cassettes. "Abortive Promoter Cassettes" or "APCs" are DNA constructs containing a natural or artificial promoter recognized by an RNA polymerase to direct Abscript synthesis. In certain embodiments, the APCs of the present invention include highly abortive natural promoters or artificial promoters that contain two regions of complementary, double strand DNA that may flank a "bubble" region of unpaired, non-complementary, anti-parallel single-strand DNA. The bubble region comprises the promoter sequence on one strand and a non-complementary DNA sequence on the other strand. The non-complementarity of the bubble region facilitates Abscription by providing access to the promoter and obviating the need for RNAP to melt and unwind DNA near the synthetic promoter.

In some embodiments, the APCs of the invention are comprised of two DNA strands that are complementary at or near their termini. Thus, the ends of such APCs of the invention have double stranded regions, which serve to join the two strands of DNA. In certain aspects, one or both strands of DNA in an APC may include a single-strand overhang for conjugation to a TSP. Thus, a typical APC includes two DNAs, however, single strand APCs that can be converted to double strand molecules (e.g. by an amplification reaction), are also contemplated by the invention.

The skilled artisan will recognize that disclosed APC structures are exemplary only, and other configurations are possible. The essential features of an APC of the present invention are a DNA containing an artificial or naturally abortive promoter-containing region (e.g., "bubble") for Abscript synthesis, a discrete template for synthesizing Abscripts of uniform size, and a means for attaching to a target site probe of the invention.

Non-limiting examples of APCs suitable for use as in the present invention, as described or with modifications appropriate to conjugation to the TSPs of the invention, are provided in Ser. No. 09/984,664 (filed Oct. 30, 2001) now U.S. Pat. No. 7,045,319; Ser. No. 10/425,037 (filed Apr. 29, 2003); Ser. No. 10/600,581 (filed Jun. 23, 2003) now U.S. Pat. No. 7,541,165; Ser. No. 10/602,045 (filed Jun. 24, 2003) now U.S. Pat. No. 7,468,261; Ser. No. 10/607,136 (filed Jun. 27, 2003), now U.S. Pat. No. 7,226,738; Ser. No. 10/686,713 (filed Oct. 17, 2003); Ser. No. 10/976,240 (filed Oct. 29, 2004); Ser. No. 10/790,766 (filed Mar. 3, 2004) now U.S. Pat. No. 7,473,775; Ser. No. 10/488,971 (filed Oct. 18, 2004) now U.S. Pat. No. 7,470,511; and Ser. No. 10/551,775 (filed Sep. 14, 2006) the contents of each of which are incorporated by reference herein in their entirety. Other APCs include natural promoters with high abortive turnover rates.

The sequences of the promoter and the initially transcribed template DNA sequence have significant effects on the lengths of the predominant abortive transcripts, as well as their rates of synthesis (Hsu (2006) Biochemistry 45:8841-54). This characteristic has been exploited to develop artificial promoters used in the APCs of the invention that are optimized to make Abscripts of different sequences and lengths at extremely high rates (>1000/min) compared to typical natural promoters. A given APC reiteratively generates a single type of short, uniform Abscript under the particular Abscription conditions selected for an assay.

Abscription can be readily adapted to high level multiplexing by varying the sequence and length of the Abscript products at the template level. Template APCs for 20 different trinucleotides with high turnover have been synthesized and at least 10 of these distinct trinucleotides can be detected in a single reaction via mass spectroscopy.

Methods for Detecting Abscripts. The signal readout is flexible with Abscription. Unlabeled trinucleotide Abscripts can be detected by HPLC, tandem HPLC-mass spectroscopy (LC-MS) or Thin Layer Chromatography. It is also possible to label Abscripts with radioactive or fluorescent labels and affinity tags on one of the incorporated nucleotides. In addition to trinucleotide Abscripts, APCs that can produce exclusively 11-nt Abscripts have been developed. This length is sufficient to allow detection based on hybridization of the Abscripts to probes such as molecular beacons. Such molecular beacons can be opened by 11-mer Abscripts in combination with primer extension.

Abscription signal generation for target detection is adequate to allow direct Abscript detection by mass spectroscopy or thin layer chromatography; radiolabeling and rapid TLC or electrophoresis; or fluorescence intensity. Abscripts can be synthesized e.g., with fluorescent labels to allow direct detection or with affinity tags to allow the attachment of a secondary signaling system such as streptavidin-horseradish-peroxidase (HRP). In certain embodiments of the invention, APCs can be integrated into primers for loop-mediated isothermal amplification (LAMP) to reduce the limit of detection (LOD) for DNA and RNA to 10 molecules per sample after 15 minutes of amplification.

Advantages of Abscription Technology.

Abscription has many advantages over target amplification and other methods for detecting mCpG. Probe development is much simpler than in bisulfite based systems. Only a single capture probe complementary to native target DNA sequence is required.

The enzyme used in PCR is easily inhibited. The usefulness of PCR for blood-based diagnostic tests is limited by the presence of several components in blood that reduce the amplification efficiency, such as hemoglobin and hemin, high concentrations of leukocyte DNA and immunoglobulin G (IgG). The usefulness of PCR for environmental and food testing is further complicated by inhibition dust, diesel soot and components found in soil, including humic acid. Samples must therefore be carefully purified to remove such inhibitors before PCR to prevent false negative results.

Unlike systems based on target amplification, there are no constraints to have individual probes function together or to fit within a minimal spacing. Promoter-directed Abscription of short, reiterative, abortive transcripts does not require primers for initial RNA synthesis. Thus, initiators for Abscription are nucleotides, dinucleotide, trinucleotides, or derivatives thereof. In Abscription-based the methods of the invention, Abscripts that are produced do not become templates for further synthesis. Therefore, any errors in synthesis are not exponentially amplified and remain undetectable.

Abscription assays are resistant to environmental inhibitors and components of bodily fluids that severely inhibit PCR as detailed below in Example 1. Hemin and hemoglobin, for example, were found to have no effect on Abscription at concentrations up to 20-fold higher than the levels that inhibit PCR. Abscription reactions spiked to 30% v/v of whole blood showed no inhibition. Thus, Abscription saves time required to remove contaminants, which is necessary when using detection methods intolerant of such contaminants.

Abscription provides multiple options for signal readout, including HPLC, mass spec, TLC, audoradiography, capillary electrophoresis and gel electrophoresis.

Detection of CpG Methylation

Overview. The present invention provides methods for detecting CpG methylation utilizing optimized methyl binding domain polypeptides. According to the present invention, Target Site Probes (TSPs) based on mCpG binding domains (MBDs) are directly or indirectly attached to a signal generator, such as an APC. MBD reagents selectively bind methylated versus non-methylated CpG dinucleotides in target DNA. Upon binding, a detectable signal is generated from the MBD reagent, which serves as an indication of CpG methylation.

In an exemplary embodiment which serves to illustrate the overall scheme for methylation detection methods of the invention, an APC-mCpG TSP binds to mCpG sites in target DNA, and detectable Abscripts are reiteratively generated upon the addition of RNAP and NTPs. In certain embodiments, a specific initiator dinucleotide (such as ApC), and/or a chain terminator (e.g., a 3'-O-Me-NTP) are substituted for NTPs (illustrated in FIG. 1). By controlling the APC template sequence, initiator and/or terminator nucleotides, Abscript signals generated are uniform transcripts, such as trinucleotides.

A method for interrogating a specific individual CpG site and a method for measuring the overall level of methylation of a CpG island is also provided. The invention provides a simple and sensitive diagnostic method for assessing CpG methylation in CpG-islands with applications in cancer screening. Methods are also provided for diagnosis of cancer, prognosis and monitoring of treatment. Methods of the invention exploit information about cancer-related methylation signatures developed by other workers for target identification.

Methyl-CpG Target Site Probes (mCpG TSPs). mCpG binding proteins have reportedly been used in detection systems. However, the focus has been largely restricted to purification steps to enrich for heavily methylated islands. The present invention utilizes these proteins as Target Site Probes (TSPs) for mCpG. When coupled directly or indirectly to APCs or other signal generation systems, the mCpG TSPs of the invention provide signal generating detectors for mCpG.

A mCpG TSP of the invention is a methyl CpG binding polypeptide, or other molecule comprising a methyl CpG binding domain (MBD). mCpG binding proteins (e.g., MeCP2, MBD1, MBD2 and MBD4) preferentially bind a symmetrically methylated CpG motif on DNA. mCpG TSPs derived from these proteins thus have the ability to discriminate between methylated, and hemi-methylated or unmethylated CpG. In one embodiment, a mCpG TSP of the invention has at least about a 10-fold preference for fully methylated DNA over unmethylated DNA. In another embodiment, the mCpG TSPs has at least about a 50-fold preference for methylated over hemi-methylated DNA. In yet a further embodiment, the mCpG TSPs has at least about a 75-fold preference for methylated over hemi-methylated DNA.

mCpG TSPs of the invention can be isolated, naturally occurring proteins, but more conveniently are synthetic polypeptides that are expressed in host cells from a recombinant DNA construct. To facilitate purification of recombinant TSPs, a mCpG binding domain (MBD) can be joined to an affinity tag as a fusion polypeptide. As used herein, "affinity tag" refers to an amino acid sequence that is engineered into or joined to a polypeptide to facilitate purification of the resulting fusion polypeptide by allowing affinity purification. Suitable affinity tags for use in the mCpG TSPs of the invention include His, CBP, CYD, Strep II, FLAG, HA, HPC, GST, and the like. In certain embodiments, the affinity tag is glutathione-S-transferase (GST), which permits purification on a glutathione resin by binding the GST affinity tag and subsequent elution with free glutathione. Where the affinity tag is not desired in the final TSP, a linker peptide containing a protease recognition site, such as a thrombin cleavage site, can be included between the MBD and the affinity tag.

In some instances, retaining an affinity tag can be advantageous. GST, for example, contains solution-available cysteine residues that can be used for conjugation to APCs or other signal detectors without disrupting the methyl-binding regions on the MBD-GST fusion polypeptides. In certain aspects of the invention, MBD-affinity tagged fusion polypeptides of the invention include at least one cysteine residue in a position that is not essential for binding of the polypeptide to methylated DNA. Such non-essential regions can include the affinity tag region, optional linkers in the fusion polypeptide and regions of the methyl binding protein outside the methyl binding domain. However, in certain aspects of the invention, cysteine or other residues in the MBD may be conjugated to APCs or other detectors without diminishing mCpG binding.

The mCpG TSPs of the invention can also be used independently of Abscription as high purity mCpG detection reagents. Thus, the present invention provides novel mCpG binding polypeptides as described above, and mCpG detectors containing such mCpG binding polypeptides linked to APCs or other groups.

The invention also provides polynucleotides encoding mCpG TSP and vectors containing the same, such as plasmid, cosmid, phagemid, viral, and other vectors that are known in the art. In certain embodiments, the mCpG TSP is expressed from the polynucleotide of the invention in a host cell, which can be any suitable cell, including but not limited to a bacterial, fungal, insect, or animal cell. Where the mCpG TSP-encoding polynucleotide includes sequences from an organism other than the expression host, it may be desirable to alter the polynucleotide sequence to include codons preferred by the host. Such changes may improve the efficiency of protein translation in the host cell, thereby improving the yield of expressed mCpG TSP. For example, where the mCpG TSP polynucleotide contains mammalian sequences (e.g. mouse or human) and the expression host is a bacterial cell, such as E. coli, the TSP polynucleotide sequence can be optimized for expression in bacteria by replacing one or more codons in the mammalian sequence with high-frequency bacterial codons. In other embodiments, at least about five codons are optimized. The invention also contemplates synthetic genes in which all codons are optimized for efficient expression in a particular host cell.

Methyl CpG Detectors.

mCpG detectors of the invention contain a mCpG TSP coupled to a detection reagent or system that is capable of generating a detectable signal. The skilled artisan will appreciate that a wide variety of signals may be used in the detection methods of the invention, including, but not limited to mass-detectable signals, color dye signals, radioactive signals, fluorescent signals, and luminescent signals.

In certain embodiments, the methyl CpG detectors of the invention rely on reiterative, abortive synthesis of uniform Abscripts from an APC, as described above, to provide a signal. Certain methyl CpG detectors of the invention contain a mCpG TSP, linked directly or indirectly to at least one APC. The TSP can be any of the mCpG-TSPs described above, such as a polypeptide containing a MBD (e.g., MBD2 or MeCP2) and optionally, an affinity tag.

In certain embodiments of the invention, the signal generator, such as an APC, is linked directly to the mCpG TSP, such as through a covalent bond between an amino acid side chain on the TSP and e.g., a primary amine group of the APC. Cysteine residues that are not involved in disulfide bonding can provide convenient sites on the TSP for attachment to an APC or other signal generator. The skilled artisan will be aware of methods for conjugating a DNA (the APC) molecule to a polypeptide (the TSP), such as by using a heterobifunctional crosslinking reagent like sulfosuccinmidyl-4[N-maleimidoethyl]cyclohexane-1 carboxylate. Preferably, the signal generator does not interfere with mCpG binding of the TSP and thus it may be desirable to conjugate the signal generator to a region of the TSP that is not essential for binding to methyl CpG. Such regions include those outside the MBD and select residues in the MBD that are not involved in direct contact with methylated DNA. In certain embodiments of the invention, multiple signal generators are linked to a single TSP to increase signal generation. In certain aspect of the invention, multiple copies of the same APC signal generator are linked to a given TSP molecule in order to generate uniform Abscript signals from that particular TSP.

In other embodiments of the invention, the signal generator can be indirectly linked to the mCpG TSP. For example, an APC can be conjugated to an antibody that recognizes the TSP, such as an antibody that recognizes the TSP affinity tag. Binding of the anti-affinity tag antibody to the mCpG TSP provides an indirect link between the TSP and the APC. This embodiment of the invention offers the advantage of conjugating signal generators to a single species that can be used for all TSPs having the same affinity tag. In similar embodiments, the signal generator can be conjugated to a ligand that binds the affinity tag, or other molecule that binds the TSP.

In an alternative embodiment, signal generators are linked to the mCpG TSP through one or more streptavidin-biotin interactions. In one aspect of this embodiment, a MBD-GST fusion polypeptide or other cysteine containing mCpG TSP is used. One, two, three, four or more biotin residues can be covalently linked to surface-exposed cysteines associated with e.g., the GST domain and the carboxyl end of the MBD. The biotin then forms an anchor for complexing detection reagents.

Figure 15:
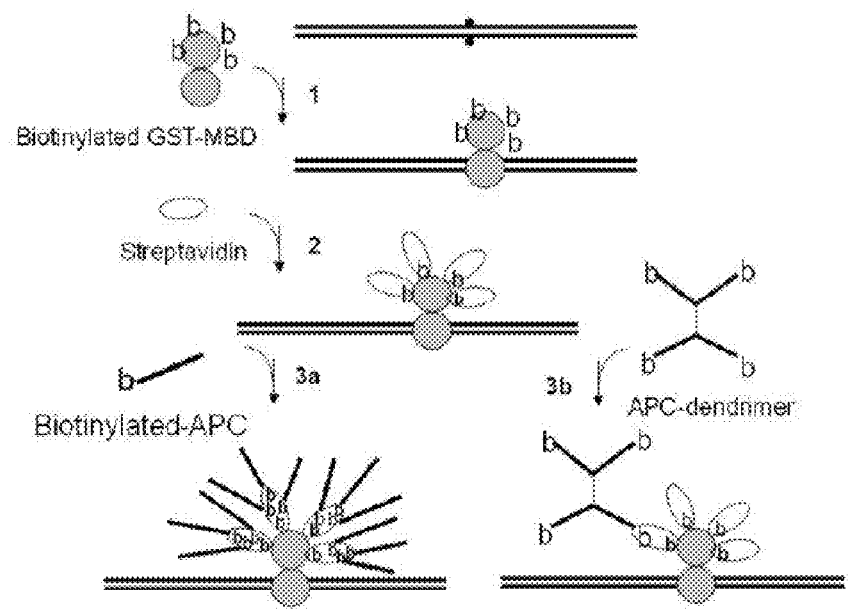
FIG. 15 is a schematic representation of a methylation detection assay using a biotinylated GST-MBD.

FIG. 15 depicts the use of such biotin residues to create a detection complex starting with GST-tagged MBDs immobilized to methylated target DNA. A biotinylated GST-MBD is first bound to methylated CpG sites on the target DNA. Streptavidin is next bound to the biotin residues on the surface of the GST-MBD. Streptavidin has 4 biotin binding sites, only one of which would be needed for attachment to the GST-MBD. Finally biotinylated APC signal generators are bound to the remaining biotin binding sites on each streptavidin. GST-MBD proteins with 4 biotins can link to as many as 12 APCs.

Even greater numbers of APCs can be attached to the streptavidin-GST-MBD complexes in the form of dendrimers. For the sake of simplicity, attachment of only one dendrimer is depicted in FIG. 15. However, multiple dendrimers can bind to the complex if multiple streptavidins are attached to the GST-MBD. APCs terminated with biotins form the branches of the dendrimer. Any one of the branches can attach to the immobilized protein via the biotin-streptavidin interaction. All of the branches can undergo Abscription to produce a uniform Abscript product at high levels.

The skilled artisan will appreciate that other oligo- and polynucleotide signal generating systems can be coupled to the TSPs of the invention. For example, a nucleic acid replication or amplification template can be substituted for the APC under appropriate conditions. According to this embodiment of the invention, a replication product signal is detected following replication of template nucleic acid in the presence of a suitable DNA polymerase, primer, dNTPs, buffer and other components that will be known to the skilled artisan as necessary for carrying out replication of the template. In certain embodiments, replication is accomplished using the polymerase chain reaction (see, e.g., Sambrook and Russell, Molecular Cloning, a Laboratory Manual, $3^{rd}$ ed., 2001). In other nonlimiting embodiments of the invention, amplification is performed by the techniques of: isothermal amplification of DNA (see e.g., PCT International Application No. WO 00/41524); Single Temperature Strand Displacement Amplification (SDA) (see e.g., U.S. Pat. No. 5,270,184); Transcription Mediated Amplification (TMA) (U.S. Pat. No. 5,766, 849); or Ligase Chain Reaction (LCR) (see e.g., Wu & Wallace, 1989, Genomics 4:560).

In other embodiments of the invention, the signal generator is an enzyme, such as horseradish peroxidase (HRP), which enzymatically catalyzes the production of colorimetrically detectable signals from well known substrates. An enzyme detector can be encoded by (i.e. as a fusion protein) or coupled directly to the mCpG TSPs described above to provide a mCpG detector. Alternatively, the signal generator can be linked to the mCpG TSPs through e.g., an antibody. Such antibodies can be directed to the MBD of the mCpG TSPs, or conveniently, can bind to the affinity tag portion of mCpG fusion protein TSPs of the invention (e.g., GST).

To enhance signal generation and facilitate use of universal reagent, such antibodies can be tagged (e.g., biotinylated) and combined with enzymes linked to affinity reagents (e.g. streptavidin-HRP). An antibody bearing multiple biotins will allow attachment of multiple streptavidin-HRPs per bound mCpG TSP. The use of a streptavidin-poly-HRP reporter allows attachment of a large number of HRPs per biotin. Assuming two antibodies per dimeric MBD protein and a minimum of three streptavidin-poly HRP complexes per antibody, up to 500 HRP reporters could be bound per bound methyl-CpG site.

Methods for Detecting mCpG

The present invention provides methods for detecting CpG methylated DNA fragments. Generally, a methylated DNA fragment is contacted with a mCpG detector that binds to at least one mCpG on the fragment, and detection of a signal from the mCpG detector indicates the presence of CpG methylation.

All of the detectors described above are contemplated for use in the detection methods disclosed herein. In certain non-limiting embodiments of the invention, which are described in detail, the detector is APC-based. According to such embodiments, Abscripts are synthesized from the APC promoter by incubation with an RNA polymerase and NTPs, and the Abscripts are detected, indicating the presence of the CpG methylated DNA. In lieu of or in addition to NTPs, Abscripts can be synthesized with specific transcription initiators (such as dinucleotides) and/or transcription terminators, such as nucleotides modified such that further elongation of the transcribed RNA is not possible following incorporation of the terminator (e.g, O-methyl nucleoside triphosphate).

Abscripts that are reiteratively generated from mCpG detectors are short, uniform abortive RNA transcripts. Abscripts synthesized from a single mCpG detector under conditions employed in the methods of the invention are uniform in size, which can be 2 to about 25 nucleotides in length, is typically 2 to about 15 nucleotides in length, and is frequently 2 to about 12 nucleotides in length. It will be apparent to the skilled artisan that the shorter the length of the Abscript, the larger the number of Abscripts that can be produced in a given time. However, longer Abscript lengths offer higher levels of detectable variation among Abscripts, which can be desirable, for example, when multiplex Abscription methods using multiple APCs are employed, or certain detection methodologies, such as molecular beacons, are used.

Abscripts size can be controlled by the sequence of the APC template, the composition of the NTPs, initiators and terminators available in during abortive transcription, or both. For example, if the initial sequence of the template is 3'-GCAT-5', but only C, G and U nucleotides are available, synthesis will be aborted after producing the trinucleotide Abscript 5'-CGU-3'. In certain embodiments, trinucleotide Abscripts are synthesized that contain only an initiator and a terminator. Such trinucleotides are readily detectable by mass spectrometry, HPLC or TLC.

In other embodiments, labeled nucleotides can be incorporated into the Abscripts, thereby allowing detection via the label. For example, the initiator, terminator or both can include a radioisotope that can be detected by thin layer chromatography or gel electrophoresis and autoradiography. Other detectable labels contemplated for use in the methods of the invention are well known in the art, including, e.g., fluorochromes, molecular beacons, and mass labels.

The methylated target DNA fragment is typically generated from a sample containing genomic DNA by restriction enzyme digestion. Methods for preparing and digesting genomic DNA with restriction enzymes are well known in the art. Samples suitable for analysis according to the methods of the invention include but are not limited to biological, clinical and biopsy specimens, such as blood, sputum, saliva, urine, semen, stool, bodily discharges, exudates, or aspirates and tissue samples, such as biopsy samples.

To facilitate analysis of a specific DNA target, the methylated DNA fragment can be captured using a probe that hybridizes to the target sequence of interest. The capture probe can hybridize to any region on the target sequence, but typically is designed to anneal to the 5' or 3' end of a target DNA fragment. Where the target DNA fragment contains a CpG island, a capture probe will typically hybridize to a nucleotide sequence adjacent to the island, or within about 10-50 nucleotides thereof. Target probes are single strand oligo- or polynucleotides that are substantially complementary to the target DNA fragment and can be from about 10 to about 100 nucleotides in length; typically about 15 to about 50 nucleotides in length and frequently about 20 to about 30 nucleotides in length. By "substantially complementary," it is meant that the probe is at least about 80%, 90%, 95%, 99% or more identical to a sequence of the target DNA fragment.

Capture is accomplished by immobilizing the capture probe to a solid support, such as a bead, tube, microtiter plate, membrane, glass slide or other support known in the art. According to one embodiment, denatured target DNA fragments are hybridized to the capture probe and then the unhybridized target DNA fragments are separated from capture probe-immobilized target DNA fragments. The skilled artisan will recognize that immobilization of the target probe can be accomplished prior to hybridization, such as by coupling or affixing the probe to the solid support. Alternatively, the probe can be immobilized during or after hybridization. For example, a biotinylated capture probe can be hybridized to the target DNA fragment in solution and then contacted with a streptavidin-coated solid support, such as streptavidin beads. In one embodiment, denaturation, hybridization and immobilization can be performed essentially simultaneously in a single tube or other vessel. For example, a target DNA fragment-containing sample, biotinylated probe and streptavidin-coated magnetic beads can be combined in a tube or other vessel and the target DNA fragment denatured by the application of heat or heat plus a chemical denaturant (e.g. guanidinium). As the mixture cools, the biotinylated probe anneals to the target DNA fragment and is immobilized to the beads, thereby capturing the target DNA fragment. The beads can then be separated from unimmobilized reagents using a magnet and washed to remove unbound reagents.

In order to detect a CpG methylated DNA fragment, the fragment is contacted with a mCpG detector of the invention that binds to at least one mCpG on the methylated DNA fragment. Because mCpG detectors based on methyl binding proteins recognize symmetrically methylated duplex CpG motifs, targets that are denatured as described above are hybridized to a synthetic, mCpG probe to convert at least one single-strand target mCpG to double-strand mCpG. The mCpG probe is complementary to the captured target DNA strand and contains one or more methylated CpGs. In certain embodiments of the invention, the mCpG probe is fully complementary to the entire length of the target and is methylated at all CpG motifs, thereby allowing detection of target DNA fragments methylated at any CpG. Alternatively, the single stand target DNA fragments can be primer extended, e.g., from the capture probe, in the presence of 5-me-dCTP as described below in Example 11. In other embodiments, the mCpG probe is complementary to a sub-sequence of the target DNA (such as a CpG island) and/or is methylated at a limited number of specific CpG dinucleotides. According to such embodiments, a target DNA fragment that is methylated at specific sites can be detected. The invention also contemplates the use of multiple mCpG probes for a single target, each complementary to a sub-sequence of the target DNA. In this way, a large number of methylation patterns on a single DNA target fragment can be interrogated using a limited set of mCpG probes in various combinations.

In certain embodiments, a double strand CpG methylated DNA fragment is captured without denaturation. Such fragments have CpGs that are methylated prior to capture and thus retain the original methylation pattern of a target sequence on both strands of duplex the DNA molecule. This method avoids the need for synthetic mCpG probes. However, only symmetrically methylated CpG sites are detected using methyl binding protein domain-containing TSPs.

In one aspect of this embodiment, a double strand target DNA fragment can be captured by exploiting the ability of the RecA protein of *E. coli* to form a filament complex with a biotinylated, single-strand capture probe in the presence of the nonhydrolyzable ATP analog 5'-[γ-thio]ATP. The capture probe filament can then form a stable triple-strand structure with the target DNA fragment, which in turn can be immobilized to a streptavidin-coated solid phase via the biotin tag on the capture probe. The capture probe is typically designed to form a triple helix with regions of the target DNA fragment adjacent to a methylated CpG island or other region of interest. According to this method of the invention, double strand methylated regions of the immobilized target are thus available for recognition by a mCpG TSP detector, as described above.

Once a mCpG detector is bound to the target CpG methylated DNA fragment, detection is accomplished via the associated signal generator as described above. For example, with APC detectors, Abscripts of a uniform size and sequence are synthesized from the APC promoter by incubation with RNA polymerase and NTPs and/or a transcription initiator and/or a transcription terminator in a suitable buffer, as described above. Detection of Abscripts synthesized provides a measure of the presence of the CpG methylated DNA fragment. For quantitative detection, the invention contemplates comparison of Abscript synthesis with negative controls (containing only unmethylated DNA) and positive controls containing fixed numbers and/or locations of mCpG motifs.

Methods for Cancer Diagnosis and Prognosis

The present invention provides methods for detecting cancer in a subject by detecting methylation or hypermethylation of a normally unmethylated or undermethylated CpG island in a sample from the subject using the mCpG TSP-detector methods described above. The cancer can, for example, be lung cancer, breast cancer, colorectal cancer, prostate cancer, bladder cancer, gastric cancer, brain cancer, renal cancer, liver cancer, or leukemia. In one embodiment, the target CpG island is in the promoter of a cancer suppressor gene. In certain embodiments, the target is a DAP kinase, p16, MGMT, or GSTP1 gene. Abscription is performed to detect mCpG in the target and the amount of methylation compared to a normal control. Detection of a higher level of methylation in the sample than in the control is indicative of cancer.

The present invention also provides methods for predicting cancer progression or outcome in a subject by detecting methylation or hypermethylation of a normally unmethylated or undermethylated CpG island in a sample from the subject using the methods described herein. In one embodiment, Abscription is performed to detect mCpG in the target and the amount of methylation compared to a normal control. In certain aspects, detection of hypermethylation of E-cadherin, DAP kinase, p16, EMP3, or calcitonin targets as compared to normal controls, is indicative of an increased risk of cancer relapse or a shorter survival.

In yet another embodiment, detection differences in the methylation state of, for example, CHFR, MGMT, COX2, ATM, phosphoserine aminotransferase, ESR1, or RASSF1A targets, as compared to normal controls, is indicative of the response of cancer to treatment.

Kits for Detecting CpG Methylation

The present invention also provides kits for detecting CpG methylation that include a container containing a mCpG detector and instructions for detecting CpG methylation using the detector. In certain embodiments, the kit also includes at least one of: an RNA polymerase, an initiator, a terminator, a capture probe or a mCpG probe. Such kits of the invention may also include positive and/or negative control target DNAs.

Also provided are reagents for detecting mCpG, such as the mCpG TSPs described herein as well as kits containing a mCpG TSP, at least one APC, and instructions for conjugating the APC to the mCpG TSP. In certain embodiments, the kit includes 2 to about 20 different APCs for multiplex CpG methylation detection.

In other embodiments of the invention, arrays are provided that include 10 to about 1000 CpG island capture probes for use in Abscription methods of the invention. The probes may be biotinylated for use with streptavidin beads or may be immobilized on the surface of a solid support, such as a microtiter plate. In certain embodiments, the capture probes of the array hybridize to a nucleotide sequence adjacent to a CpG island. Such probes may, for example, be useful for cancer screening where the target CpG islands are located in a cancer suppressor gene, proaptotic gene or DNA repair gene.

EXAMPLES

Example 1

Resistance of Abscription Assay to Inhibitors

Figure 2:
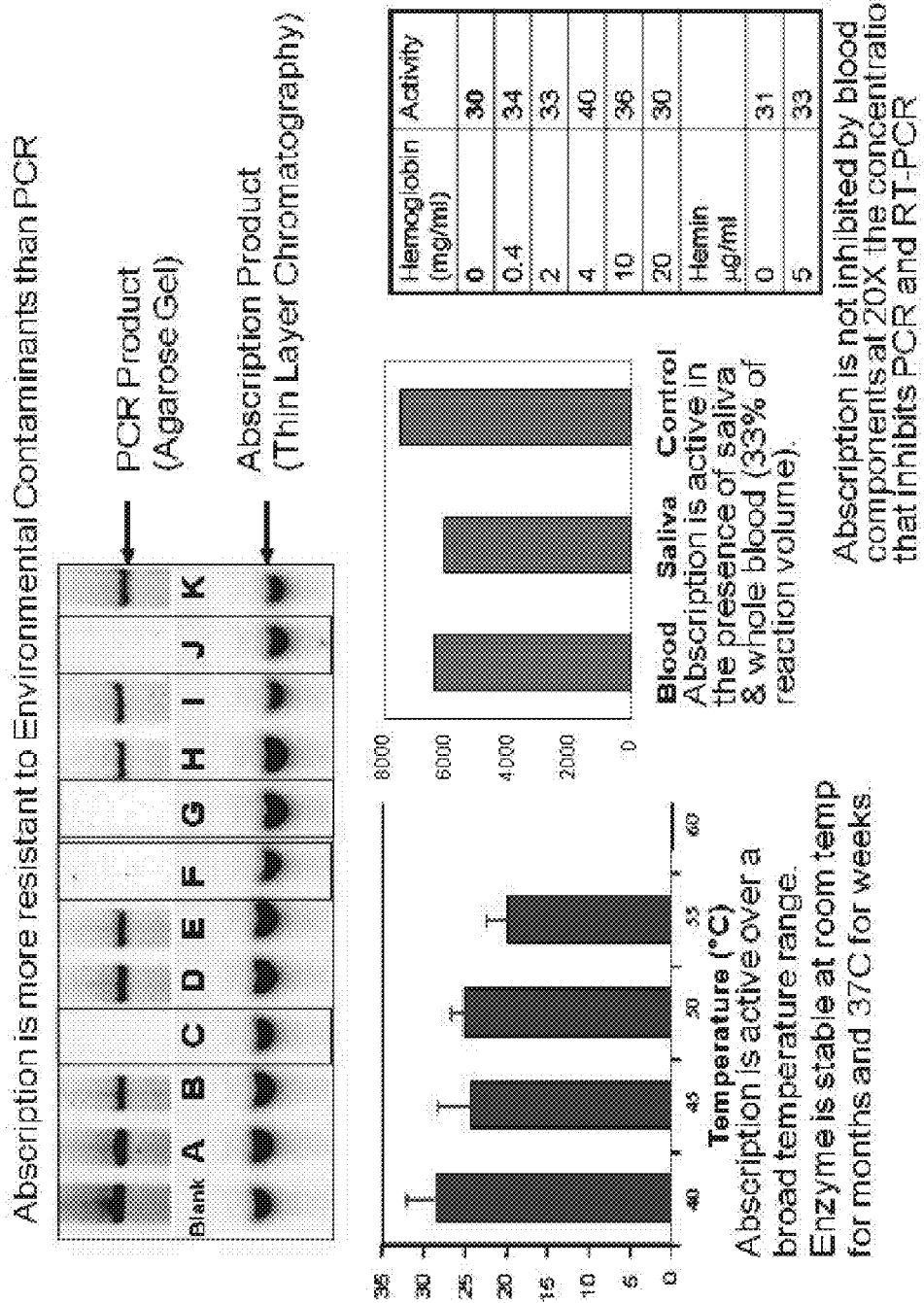
FIG. 2 is a comparison of the sensitivity of PCR and Abscription to environmental contaminants and summarizes the effects of hemoglobin, hemin, blood, and saliva on Abscription.

Abscription (performed as previously described; see e.g. U.S. Pat. No. 7,045,319) was compared to PCR in the presence of a panel of inhibitors. As shown in FIG. 2 (top bands), PCR reactions were inhibited by several types of contaminants while Abscription was resistant to all (bottom bands).

In a separate series of experiments, Abscription was challenged by addition of both hemin and hemoglobin at concentrations 20 times higher than inhibit PCR, or with pure blood to 33% (v/v) and saliva. Abscription remained active under all conditions.

Example 2

GST-MeCP2 Fusion Polypeptide and APC Conjugates

Figure 3:
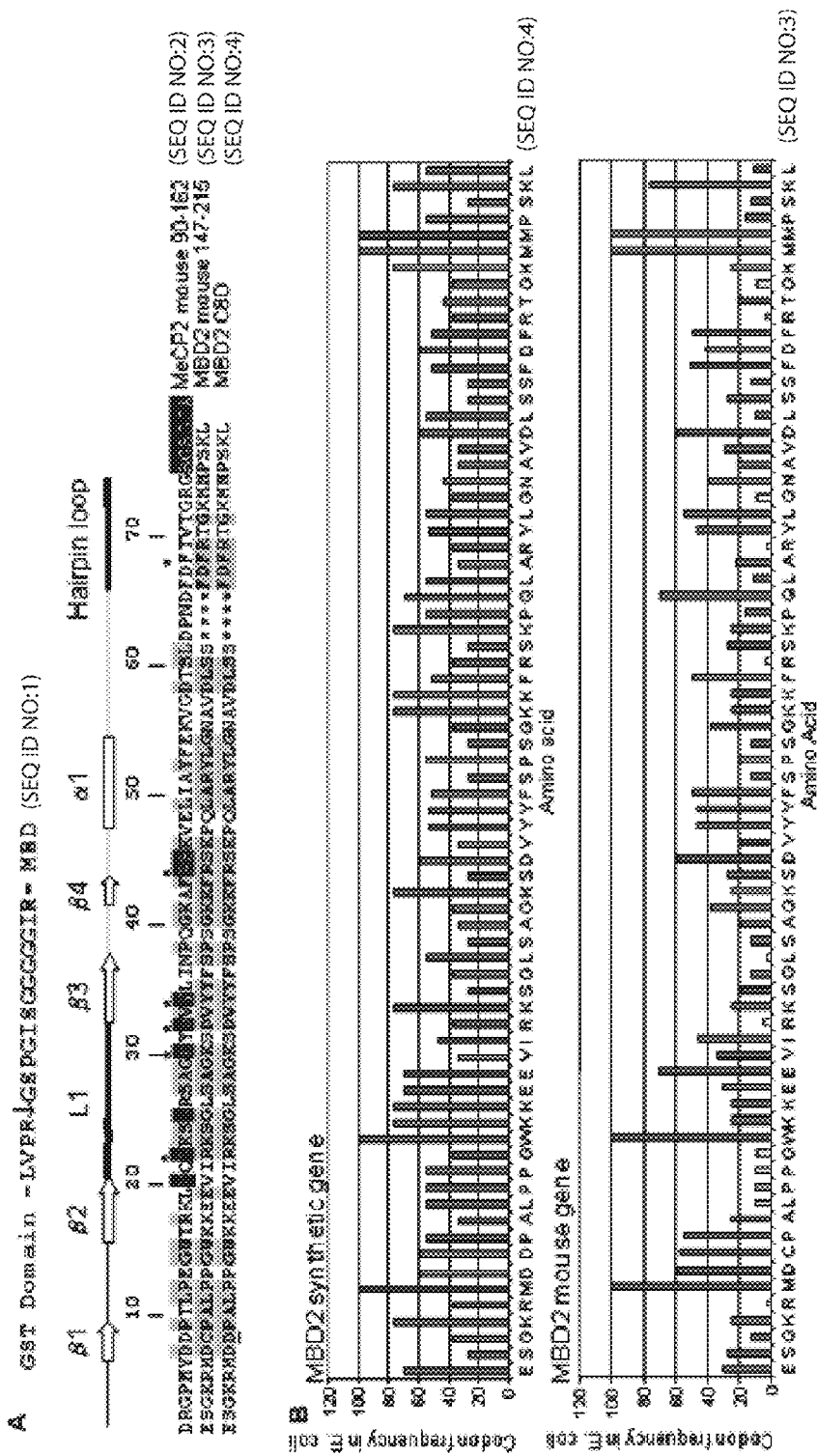
FIG. 3A shows the amino acid sequence and location of structural motifs for the mouse MeCP2 and MBD2 methyl binding domains and replacement of Cys-8 with Asp in the synthetic gene. Also shown is the amino acid sequence of the linker in a GST fusion polypeptide.
FIG. 3B illustrates the E. coli codon frequency of amino acids in the mouse MBD2 methyl binding domain and in an synthetic methyl binding domain optimized for expression in E. coli.

Design and Preparation of a Synthetic GST-MeCP2 Polynucleotide. A synthetic, truncated gene for MeCP2 was designed to allow attachment of an APC to a nonessential site immediately adjacent to the DNA binding domain of MeCP2. FIG. 3 shows the amino acid sequence of the mCpG binding domain (MBD) of the MeCP2 protein (Nan et al. (1993) Nucl. Acids Res. 21:4886-92). Structural features are indicated above the sequence in FIG. 3.

The first 70 amino acids have been reported to be sufficient for recognition of mCpG sites. In addition to the first 70 amino acids, the synthetic gene included a Cys codon near the carboxyl end to allow attachment of a sulfur-reactive APC (FIG. 3). The Cys-containing amino acid sequence is not encoded by the gene for the native protein and was arbitrarily introduced into the synthetic gene to allow attachment of affinity tags and APCs even when the GST affinity domain is removed. Placement of the APC was guided by the solution structure of the MeCP2 mCpG MBD. NMR studies have indicated that both the N- and C-terminal regions are unstructured (Wakefield et al. (1999) J. Mol. Biol. 291:1055-65). However, the N-terminus has been reported to participate in the formation of protein-DNA complexes. Thus, the C-terminus was chosen for linkage to the APC. Furthermore, mutagenesis in combination with binding studies of MeCP2 and MBD 1 implicated specific residues for direct DNA interaction in β2-β4. (Free et al. (2001) J. Biol. Chem. 276:3353-60; Ohki et al. (2001) Cell 105:487-97; Ohki et al. (1999) EMBO J. 18:6653-61). The site for APC placement was located as far as possible from these sites.

For high-level expression in *E. coli*, the synthetic gene was designed with codons optimized for expression in *E. coli* in preference to subcloning from the mouse cDNA. The N-terminal half of mouse MeCP2 has 5 Arg residues, which in mouse are encoded by codons that are rarely used in *E. coli* (Kane (1995) Curr. Op. Biotech. 6:494-500). These codons were replaced with counterparts preferred in *E. coli* to improve translation efficiency and thereby increase expression.

The synthetic MeCP2 methyl binding domain gene was fused to the glutathione-S-transferase gene by cloning into a pGEX vector to create pMECP2. The linker between the GST and the binding domain contains a thrombin cleavage site (FIG. 3) and a poly Gly sequence to promote efficient thrombin cleavage (Guan & Dixon (1991) 192:262-67). Cloning into pGEX placed the hybrid gene under control of the Ptac promoter, which is repressed by a lacI$^q$ gene located on the same plasmid (Guan & Dixon (1991) 192:262-67). Thus, expression of the fusion polypeptide was inducible with IPTG.

Expression and Purification of the GST-MeCP2 MBD Polypeptide. A 500 ml BL21(lon⁻, ompT⁻)/pMECP2 culture was induced with IPTG in log phase ($OD_{600}$=0.4) and incubated for 3 hours at 30° C. before lysis by sonication. The soluble fraction was purified on a reduced glutathione-agarose column. No attempt was made to determine the relative amounts of fusion polypeptide in the insoluble verses soluble fractions. The estimated yield in the soluble fraction was about 1 mg/ml of crude lysate, allowing production of the polypeptide economically in large amounts from the soluble fraction alone. The linkage between the GST domain and the MeCP2 MBD was retained so that Cys residues in the GST domain could be exploited for conjugation to APC. Quantitative separation of the GST and the binding domain could be achieved by treatment of the eluted polypeptide with a thrombin-agarose resin.

APC conjugation of GST-MeCP2. The existing Cys site in the carboxyl end of the MeCP2 MBD and the Cys residues in the *S. japonicum* GST were targeted for covalent linkage to a duplex DNA APC containing a maleimide at the 5' end of the nontemplate strand of the APC. A synthetic nontemplate strand with a 5' primary amine was annealed to a complementary template strand, and then the duplex was incubated with the heterobifunctional crosslinker SMCC (sulfosuccinimidyl-4[N-maleimidoethyl]cyclohexane-1 carboxylate; Pierce, Rockford, Ill.). The amine-reactive NHS ester linked the maleimido group to the 5' end of the APC. SMCC-treated APC DNA was desalted by passage through a size exclusion resin to remove excess SMCC.

Approximately 0.5 mg of GST-MeCP2 hybrid was immobilized to reduced glutathione-agarose resin directly from a crude lysate. The beads were washed and resuspended in 3 ml of maleimide-tagged APC followed by incubation at 25° C. for 1 hr and overnight storage at 4° C. The resin was then packed into a column and washed with PBS before eluting the polypeptide with buffer containing 20 mM reduced glutathione. Nearly half of the eluted polypeptide exhibited slower electrophoretic mobility than GST-MeCP2 indicating conjugation to an APC. The presence of multiple shifted bands suggests that a fraction of the conjugates contain more than one APC. The 3-dimensional structure of *S. japonicum* GST shows that 3 of the 4 cysteines in GST sequence are accessible at the surface and none are involved in disulfide linkages. The MeCP2 domain has an exposed cysteine near the carboxyl end of the polypeptide which should also be accessible to the APC-crosslinker. The GST-MeCP2 fusion polypeptide is, therefore, predicted to have 4 Cys residues available for conjugation. Thus, APC-fusion polypeptide conjugates may have as many as 4 APCs.

Example 3

GST-MBD2 Fusion Polypeptide and APC Conjugate

Design and Preparation of a Synthetic GST-MBD2 Polynucleotide. MBD2b has the highest affinity for mCpG sites and the lowest cross reactivity with unmethylated CpGs among the known methyl CpG binding proteins. These differences are particularly large in comparison to mouse MeCP2, where the differences in affinities for methylated islands between the two proteins reportedly range between 24 and 100 fold (Fraga et al. (2003) Nucl. Acids Res. 31: 1765-74). MBD2b also has a higher bias in favor of methylated DNA over unmethylated DNA compared to mouse MeCP2 (70 fold verses 2.7 fold) (Fraga et al. (2003) Nucl. Acids Res. 31:1765-74).

These differences in sensitivity and preference for methylated DNA could be partially explained by an additional MeCP2 requirement for an uninterrupted string of four As and Ts close to the targeted mCpG site. The affinity measurement noted above was performed with DNA that lacked this sequence feature (Fraga et al. (2003) Nucl. Acids Res. 31:1765-741; Klose et al. (2005) Mol. Cell. 19:667-78). Even if MeCP2 has greater affinity for mCpG sites with the optimal sequence context, it may be more limited than MBD2 as a general probe, because its affinity will vary depending on the sequence of the targeted CpG islands.

A synthetic GST-MBD2 wild type gene (sequence shown in FIG. 3A) was prepared and cloned into the pGEX as described above in Example 2 for the synthetic GST-MeCP2 gene.

The MBD2 sequence is very similar to the MBDs of MeCP2 and other methyl CpG binding proteins. Amino acid identities to the MBDs of other methyl CpG binding proteins are shaded in FIG. 3A. MBD2 has a cysteine at position 8 which could potentially undergo crosslinking to the thiol-reactive APC. To avoid this possibility, this residue could be replaced with an Asp, which is present at this site in MeCP2 and several other methyl CpG binding proteins.

Mouse MBD2 is relatively rich in codons that are translated inefficiently in *E. coli* (FIG. 3B). Codons 11-14 in the MBD2 cDNA, in particular, may be less efficiently translated in *E. coli*. In order to minimize unfavorable codon bias of MBD2 in *E. coli*, and thereby maximize expression, synthesis and construction of an MBD2 MBD gene can be performed as described for MeCP2 (Example 2), using with the codon substitutions shown in FIG. 3. The synthetic gene would then be fused to the *S. japonicum* GST gene using the linker sequence as described in Example 2.

Expression and Purification of GST-MBD2 Polypeptide. A plasmid construct containing the GST-MBD2 wild type gene was used to produce the GST-MBD2 fusion polypeptide in *E. coli* and the fusion polypeptide was purified using glutathione-agarose chromatography as described in Example 2. A 500 ml culture was induced with IPTG to produce the fusion polypeptide.

Figure 4:
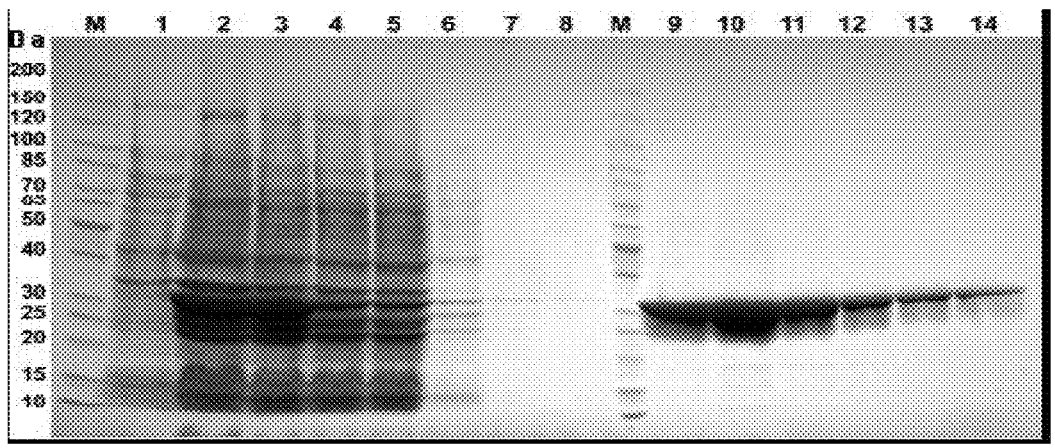
FIG. 4 is a polyacrylamide gel of samples taken during the expression of a GST-MBD fusion polypeptide and purification by glutathione-agarose column chromatography.

The GST-MBD2 fusion polypeptide was purified by glutathione-agarose chromatography, as shown in FIG. 4 (15 µl samples of the fractions run on a 4-20% SDS polyacrylamide gel and stained with Coomassie Brilliant Blue). Lane 1 shows an uninduced sample of control bacterial culture. The sonicated lysate (lane 2) was centrifuged at 10,000×g for 30 min and the supernatant (lane 3) was passed through a 5 ml glutathione-agarose column 2 times. Lanes 4 and 5 represent the depleted flow through fraction after each passage through the resin. Lanes 6-8 represent wash fractions resulting from the passage of elution buffer lacking glutathione. The fusion polypeptide was eluted in 5 ml fractions with a high salt (500 mM NaCl) buffer containing 20 mM glutathione (lanes 9-14).

Preferential Binding of Methylated DNA by GST-MBD2 Fusion Polypeptide. A preliminary titration of the GST-MBD2 fusion polypeptide against a methylated and an unmethylated 20 nucleotide oligonucleotide indicated that the best tradeoff between signal and background was obtained at a protein concentration of 3 nM. Initial experiments to determine whether the polypeptide had a preference for methylated over unmethylated DNA used DNA attached to magnetic beads. GST-MBD2 was incubated with 550 bp segment of the p16 CpG island that was either a fully methylated, or unmethylated. The DNA segment was immobilized on magnetic beads which were then blocked. Binding reactions containing 3 nM GST-MBD2 fusion polypeptide were performed for 1 hr at 25° C. followed by 3 washes with 1×PBS, 0.02% (v/v) Tween-20. The beads were then incubated with an anti-GST antibody conjugated to horseradish peroxidase (HRP). HRP signal generation was performed for 5 min at 25° C.

Figure 5:
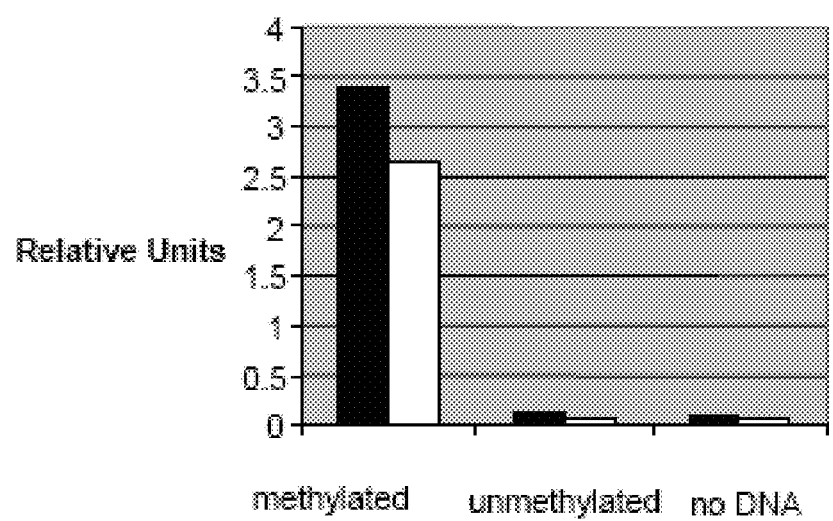
FIG. 5 shows the preference of GST-MBD for methylated versus unmethylated DNA.

FIG. 5 shows that the GST-MBD2 polypeptide has a strong preference for methylated DNA over the unmethylated DNA. Filled and unfilled bars in FIG. 5A represent duplicate measurements. The magnitude of this preference is underestimated because at this amount of methylated DNA is close to saturation.

Figure 6:
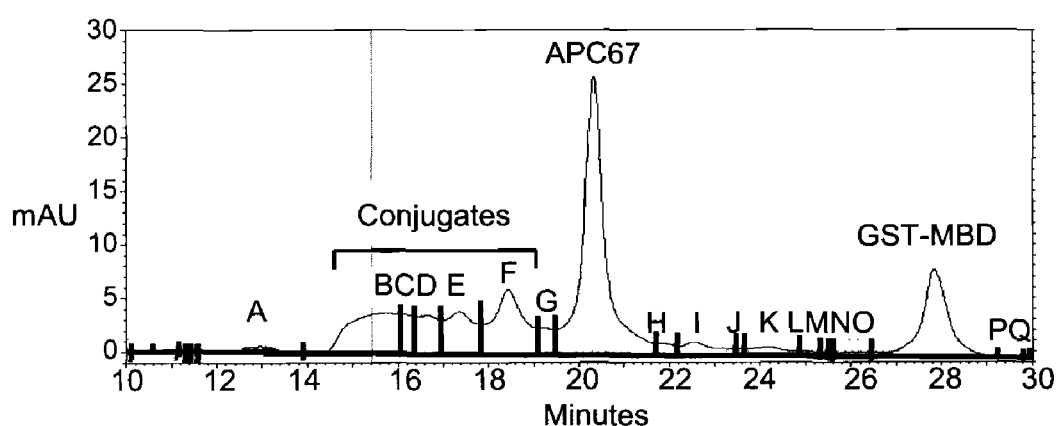
FIG. 6 is a graph representing fractions from a size exclusion fractionation of a conjugation reaction between an APC and GST-MBD polypeptide. A-Q represent the following retention times in minutes of the points indicated in the graph: A=12.950; B=15.700; C=16.133; D=16.650; E=17.367; F=18.433; G=19.233; H=21.767; I=22.550; J=23.517; K=24.183; L=24.917; M=25.367; N=25.350; O=26.067; P=29.317; and Q=29.850. The APC67 had a retention time of 20.317 minutes, while GST-MBD had a retention time of 27.833 minutes.

APC conjugation of GST-MBD2. A sulfur reactive APC (APC67) containing a 5' maleimide group was conjugated to GST-MBD2 that was immobilized to glutathione-agarose beads. Following the conjugation reaction, the resin was poured into a column and the free APC67 was largely removed with 4 column volumes of 1×PBS. The washes were performed until the absorption at 260 nm reached baseline. The polypeptide was then eluted with a high salt buffer containing 20 mM glutathione. FIG. 6 represents the fractionation of the eluted protein preparation by size exclusion chromatography to separate polypeptide-DNA conjugate from unmodified polypeptide. The retention times of the APC and unmodified GST-MBD2 were determined separately with purified APC67 and GST-MBD2 standards. No peaks with retention times similar to the conjugates were seen in chromatographs of the standards.

Preliminary results suggested that almost all of the conjugation events involve the MBD domain. However, the appearance of multiple peaks corresponding to the conjugate is consistent with the availability of multiple cysteines in the dimeric protein (8 associated with the 2 GST domains and 1 within each of the MBD domains). This chromatographic pattern is consistent with a ladder of 3 slow-mobility DNAs observed in a nondenaturing polyacrylamide gel. The separation of the conjugates from the unmodified protein is large enough to ensure complete removal of the unmodified GST-MBD2 from the final conjugate preparation.

While the amount of free APC is greatly reduced by the size exclusion chromatographic procedure, PBS washes did not quantitatively remove all of the free APC (FIG. 6). Subsequent experiments (not shown) demonstrated that residual APC can be removed by washing the column with elution buffer containing 500 mM NaCl and lacking glutathione.

Example 4

Solution Conjugation of APC-MBD Complexes

The cysteines in the GST domain to which APC molecules are conjugated are presumed to be more accessible to APC when the GST-MBD fusion polypeptide is not bound to glutathione-agarose beads. The three solvent-accessible cysteines on the GST domain are not as efficiently labeled in the solid state approach (described above) presumably due to steric hindrance caused by the proximity of the GST to the bead surface. An alternative approach to conjugation of APC to GST-MBD involves conjugation of the fusion polypeptide and the APC in solution. The advantage of this approach is that the GST-MBD could potentially be labeled with up to four APCs, thereby increasing the sensitivity of the Abscription assay. This approach has the disadvantage that a more thorough purification of the fusion polypeptide is required prior to APC conjugation and removal of un-reacted APC from conjugates is more complicated. However, a solution conjugation method leading to a heavily labeled probe may be desirable in situations where detection of single methylation event is detected.

Solution conjugation begins with GST-MPB from the lysate of a 500 ml culture of *E. coli* BL21 containing a GST-MBD expression plasmid, as described above in Examples 2 and 3. The fusion polypeptide is then extensively purified by glutathione-agarose column chromatography using a reduced glutathione elution. Following elution, the polypeptide is desalted to remove the glutathione which would compete with the polypeptide for crosslinking with the maleimide-APC. The purification results in a preparation of GST-MBD in conjugation buffer (PBS, 10 mM EDTA).

The solution conjugation is performed in the same buffer system and the same ratio of APC to fusion polypeptide (6:1) and the same reaction time as the solid-state conjugations described above in Examples 2 and 3.

Removal of excess, unreacted APC is accomplished by ammonium sulfate precipitation of the polypeptide conjugate.

Example 5

Removal of Unconjugated Fusion Polypeptide from APC Conjugation Reactions

Unconjugated fusion polypeptide is removed by size exclusion chromatography, which takes advantage of the increased size of the conjugate due to the attachment of the APC.

Optionally, the unconjugated fusion polypeptide is separated from APC-MBD conjugates by anion exchange chromatography using DEAE-resin, which exploits the large increase in negative charge on the APC conjugates. Conjugation mixtures are loaded onto a DEAE column at an ionic strength that will allow the unconjugated polypeptide to flow through the column, but retain the conjugates via the APC. The conjugate is then eluted in buffer of increased ionic strength.

Example 6

Labeling GST-MBD with Fluorescein Through Cysteine Residues

Figure 7:
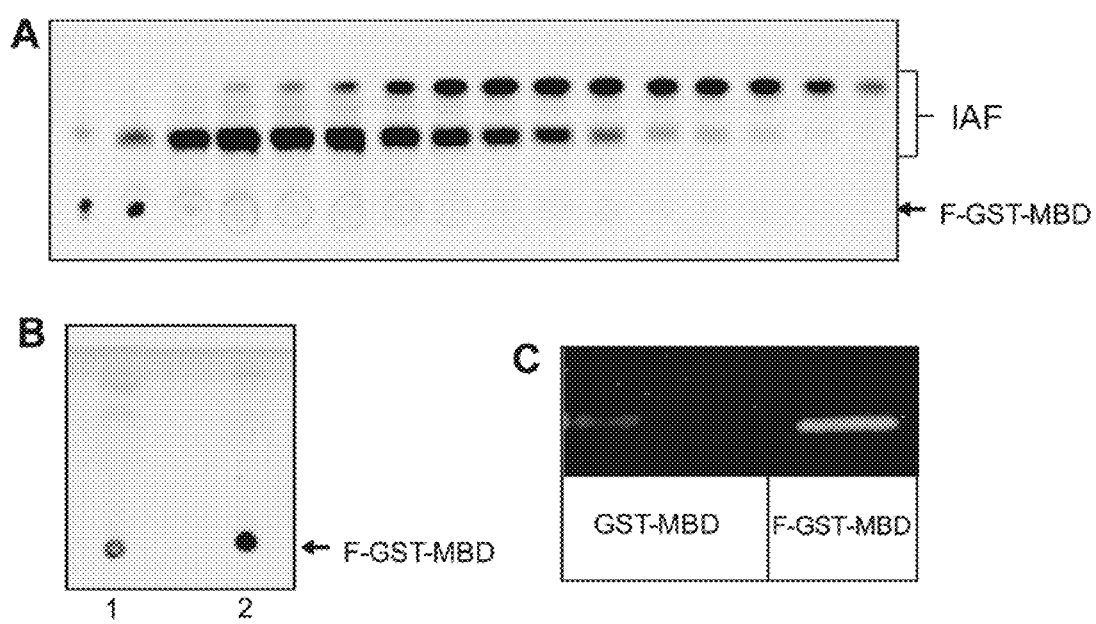
FIG. 7A shows fractions of a fluorescein labeling reaction of GST-MBD separated by size exclusion chromatography.
FIG. 7B shows TLC analysis of unbound (B1) and bound (B2) fractions of the fluorescein labeling reaction purified using glutathione-beads.
FIG. 7C shows fractionation of the purified protein (B2) from FIG. 7B by SDS polyacrylamide gel electrophoresis.

Available cysteines in the GST domain of GST-MBD are attractive targets for coupling to labels other than APCs. In this Example, the ability to conjugate fluorescently label GST-MBD through reactive cysteine residues was demonstrated. Briefly, reduced GST-MBD was incubated with thiol-reactive 5-iodoacetamidofluorescein (IAF; Molecular Probes, Eugene, Oreg.) according to manufactures directions, and the labeled protein was purified from the unincorporated label by (FIG. 7A) size exclusion chromatography and (FIG. 7B) fractionation using glutathione-beads. Fractions in panels A and B were analyzed by TLC. Labeled protein remained at the origins while the free label migrated toward the tops of the plates. Sample B1 is the supernatant of the bead-binding reaction and Sample B2 represents the protein that was bound to the beads and released with glutathione. FIG. 7C shows fractionation of the purified protein in B2 by SDS polyacrylamide gel electrophoresis. The lanes labeled GST-MBD indicate the mobility of Coomassie-Blue stained unlabeled protein. The lane labeled F-GST-MBD shows fluorescein fluorescence of the labeled protein with the same mobility as the unlabeled protein.

Example 7

Removal of GST-Domain

In some experiments, the GST domain is removed from fusion polypeptides by thrombin cleavage. The cleaved reagent is useful in situations where a lower level of APC conjugation can be tolerated, while a minimally sized MBD reagent is desirable. For example, where detection of the overall level of methylation in an entire CpG island is required (particularly where the island contains heavily methylated, closely-packed methylation sites), a minimally sized probe will be packed more densely on a target molecule than the larger, intact fusion polypeptide. The cleavage reaction is performed using a bead-linked thrombin to avoid an additional purification step.

Example 8

Indirect Conjugation of GST-MBD Fusion Polypeptides Via Anti-GST-Antibody-APC Reagents An alternative approach to direct conjugation of GST-MBD fusion polypeptides is to use an anti-GST-antibody-APC reagent. As used the Abscription assays described below, GST-MBD is bound to methylated DNA, followed by binding of the antibody-APC and Abscription from the APC. The antibody-APC approach offers the advantage that anti-GST based APCs can be used as universal signal generation reagents in conjunction with any GST hybrid binding polypeptide. This approach is also advantageous in situations where direct attachment of the APC to the MBD is undesirable, such as where direct conjugation reduces the kinetics or efficiency of DNA binding.

The procedure for conjugating APCs to antibodies is more complex than the method for conjugation to GST-MBD fusion polypeptides. An additional protein modification step is introduced involving the addition of protected thiols to the antibody with the heterobifunctional crosslinker SATA (N-Succinimidyl-5-acetylthioacetate) (Duncan et al. (1983) Anal. Biochem. 132:68-73). SATA reacts with primary amines on the polypeptide via an NHS ester. The protected thiols are deprotected by treatment with hydroxylamine. The attachment of the maleimide tagged APC is performed as described for the solution based conjugation of the GST-MBD fusion polypeptides. Removal of free APC and unconjugated antibody is accomplished by size exclusion chromatography and optionally by differential ammonium sulfate precipitation. The latter method offers the additional advantage of removing unconjugated antibody.

Example 9

Assay for mCpG Binding

The general procedure for performing Abscription assays has previously been described in Ser. No. 09/984,664 (filed Oct. 30, 2001) now U.S. Pat. No. 7,045,319; Ser. Nos. 10/425, 037 (filed Apr. 29, 2003); 10/600,581 (filed Jun. 23, 2003); 10/602,045 (filed Jun. 24, 2003); 10/607,136 (filed Jun. 27, 2003), now U.S. Pat. No. 7,226,738; Ser. Nos. 10/686,713 (filed Oct. 17, 2003); 10/976,240 (filed Oct. 29, 2004); 10/790,766 (filed Mar. 3, 2004); 10/488,971 (filed Oct. 18, 2004); and 10/551,775 (filed Sep. 14, 2006); the contents of which are incorporated by reference herein in their entirety. For detection of CpG methylation using LC-MS, the Abscription assay is performed with approximately 100-500 amoles of target DNA to ensure that sufficient signal is available. Because the Abscription assay synthesizes detectable Abscripts from only the promoter-containing template strand of DNA, signal is generated linearly at rates between 1000-2000 Abscripts/min. The sensitivity of the Abscription assay is therefore lower than that achieved with some amplification methods, such as PCR Target capture and binding of the mCpG probe are performed simultaneously. A time course for capture is performed for each probe-target combination to determine the minimal time required to assemble the methylated substrate. The kinetics of hybridization is driven by the concentration of capture probe on the beads, which is typically 2 pmoles. A one hour incubation is usually sufficient to capture more than 90% of the target strand.

The readout for target immobilization employs control TSP-APC and Abscription. The LC-MS signal is calibrated with an independent titration of the control APC. The Abscription reaction can be extended to extremely long times (e.g. overnight) if necessary to quantify the amount of target captured after short incubations.

Figure 8:
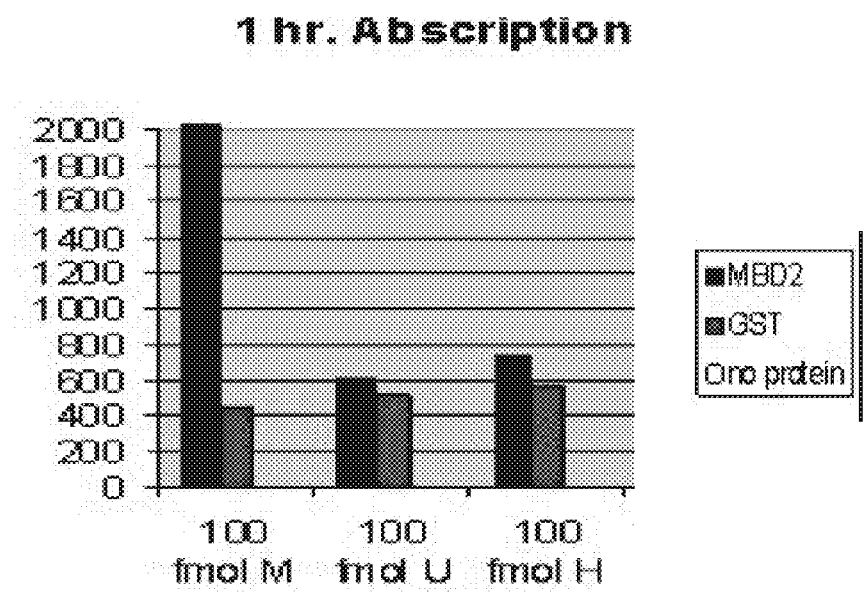
FIG. 8 shows the preferential detection of methylated (M) DNA over unmethylated (U) and hemi-methylated (H) DNA by the APC-GST-MBD fusion protein.

Controls for assessment of mCpG binding are performed using a synthetic target DNA based on a naturally occurring CpG island that has methylated CpGs at defined sites. Fully methylated, hemi-methylated and unmethylated duplexes are evaluated (FIG. 8) The binding of the GST-MBD fusion polypeptides is visualized with an anti-GST-antibody conjugated to HRP. The 70 nt segment of the CDKN2a (P16) CpG island from exon 1 is used because it has been studied intensively by other workers. The assay is performed in bead based format. A biotinylated capture probe is immobilized to magnetic beads. The synthetic single-stranded control DNA is assembled and immobilized to the beads via the capture oligonucleotide. A DNA probe complementary to the target DNA and containing one or more methylated CpG sequences is hybridized to the immobilized target, thereby permitting detection of the methylation status of particular sites. A probe containing a single methylated CpG is used to establish a concentration that gives half maximal binding ($EC_{50}$) from a saturation titration curve. The fusion polypeptide is titrated against a fixed amount of fully methylated DNA. The level of background signal is determined with hemi-methylated and unmethylated DNA by titrating the polypeptide against a fixed amount of unmethylated probe DNA. The upper concentration limit for the polypeptide probe is determined by the assay response to these control DNA target/probe combinations. Published reports indicate a 50-125 fold bias in favor of fully methylated DNA versus unmethylated DNA for MBD2b (Fraga et al. (2003). Nucl. Acids Res. 31: 1765-74). Results in the Abscription assay approximating this bias indicate that the positive and negative controls are working properly.

Example 10

Isolation of Methylated p16 CpG Island DNA and Detection by Abscription

Figure 9:
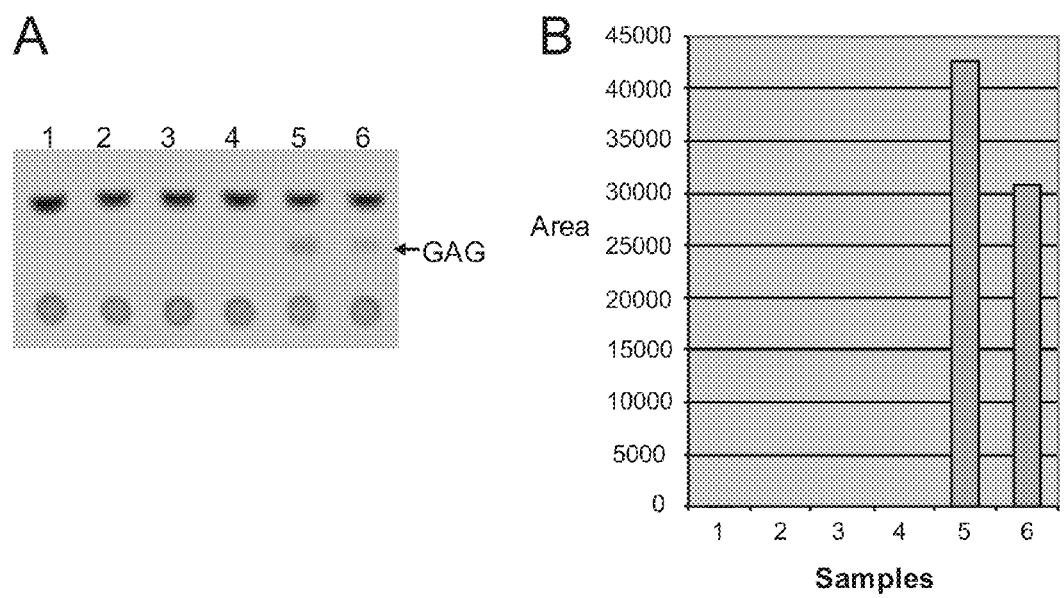
FIG. 9 shows detection of p16 CpG by abscription. Trinucleotide GAG abscripts produced from a mCpG assay were detected by TLC (FIG. 9A) or by LC-MS (FIG. 9B).

Artificially methylated Hela DNA (5 ng) was captured onto GST-MBD magnetic beads followed by three wash steps to remove residual unmethylated DNA. The methylated DNA fraction was released in two extractions with an elution buffer containing glutathione. The level of methylated p16 island sequence was determined by abscription after amplifying a segment of the p16 island with a primer pair that included an inactive single-stranded APC sequence. Amplification converted the APC into an active duplex form. An abscription reaction following amplification produced the trinucleotide GAG abscript in fractions that contained amplified p16 DNA. As illustrated in FIG. 9. FIG. 9A shows detection of the GAG abscripts produced from GST-MBD wash and elution fractions by TLC, while FIG. 9B shows the same abscript as detected by LC-MS. Lanes: 1. Unbound DNA fraction, 2. First wash, 3. Second wash, 4 Third wash, 5. First elution, 6. Second elution.

Example 11

MBD-APC Mediated Detection of CpG Methylation in CpG Islands

In this Abscription based mCpG assay (illustrated in FIG. 10), target capture is accomplished with a CpG island-specific capture oligonucleotide that is immobilized to magnetic beads. The capture probe is biotinylated and bound to streptavidin-beads. The assays are performed in a tube format or in a 96 well microtiter plate in conjunction with a plate magnet. The probe targets a sequence adjacent to a CpG island of interest. Each capture probe is specific to a single CpG island target.

Target DNA. Duplex target DNA from various biological sources is isolated and cleaved with a restriction endonuclease. The restriction endonuclease is selected based on the known location of specific CpG islands within the resulting restriction fragment. For synthetic control DNAs, this step is omitted. Target DNA fragments are then denatured at a relatively low temperature (42° C.) in combination with guanidinium isothiocyanate to avoid melting the polystyrene core of the magnetic beads and to maintain streptavidin in a native folded state. The exemplary control capture probe has a $T_m$ of 67° C. in 50 mM $Na^+$ although the polystyrene will melt at temperatures above 50° C. Capture of denatured target DNA fragments is performed by hybridizing to a labeled capture probe and binding label to affinity magnetic beads (FIG. 10, steps 1-2).

MBDs generally require double strand DNA that is methylated on the C residues of both strands of the CpG dinucleotide. Therefore, following capture, the denatured methylated target strand is converted to a duplex by hybridization of a mCpG-containing synthetic nucleotide or oligonucleotide probe (FIG. 10, step 3). This probe can contain a single methyl-C when target DNA contains a particular CpG site that is to be interrogated, or the probe can bear multiple methyl-Cs to generate a signal indicating the overall level of methylation in the target.

Figure 10:
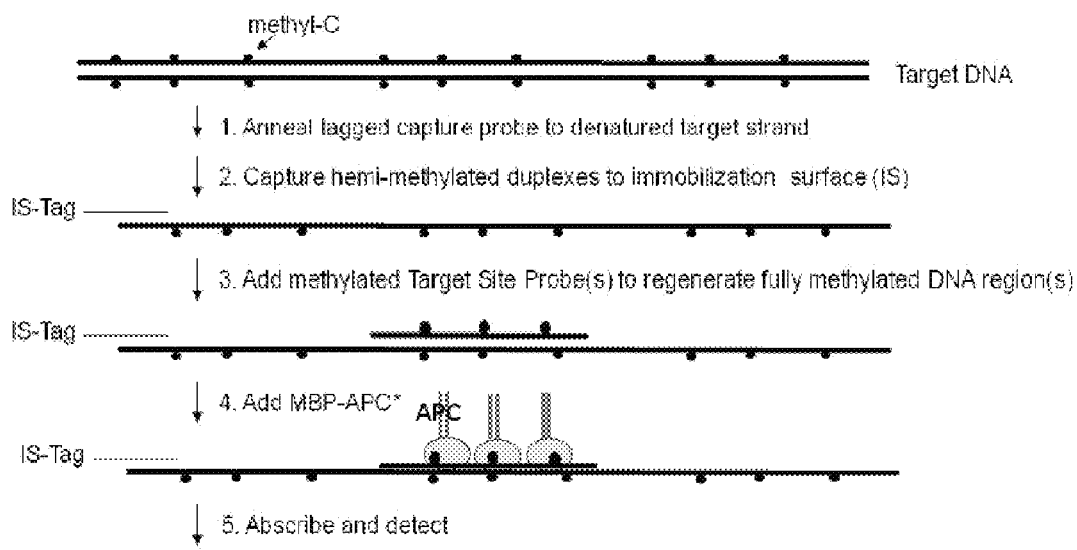
FIG. 10 illustrates the steps in an Abscription method for detecting methylation of a region of a target DNA fragment using affinity-labeled unmethylated capture probes bound to a solid support and methylated CpG region target site probes.

After a wash step to remove the hybridization buffer and unbound reagents, the MBD-APC fusion polypeptide reagent is bound to the immobilized target DNA (FIG. 10, step 4). RNA polymerase and Abscription buffer are added to commence signal generation (e.g., trinucleotide Abscripts; FIG. 10, step 5). Unlabeled Abscripts are detected by LC-MS or Thin Layer Chromatography and UV shadowing for fluorescence.

Figure 11:
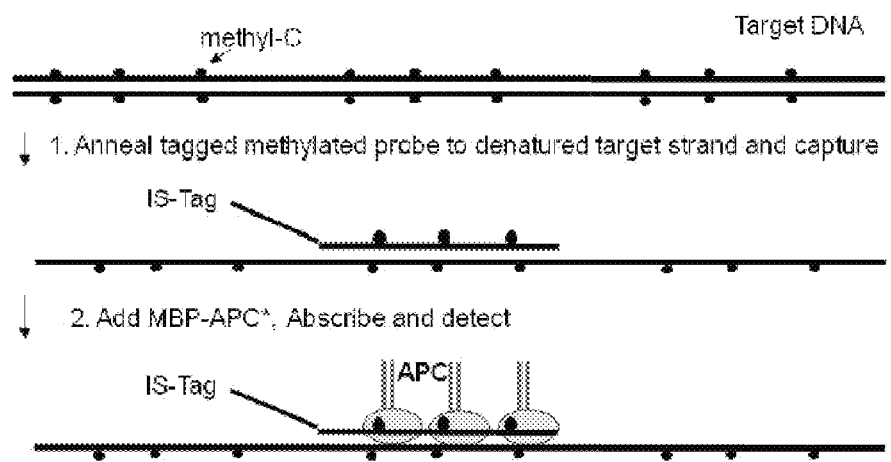
FIG. 11 illustrates the steps in an Abscription method for detecting methylation of a large region of a target DNA fragment using capture probes immobilized on a solid support and using 5-me-dCTP incorporation by primer extension of the capture probe.

An alternative approach in which target DNA is first captured as described above and then affixed directly to a solid support containing a methylated probe is outlined in FIG. 11.

Example 12

Site-Specific Assay for mCpG Using GST-MBD Conjugates

The experiment is performed to determine whether there are negative effects of the attachment of an APC to the MBD2. The results of the binding experiments with the APC conjugate are compared to experiments with the unmodified fusion polypeptide. The optimal concentration of MBD-APC is based on the tradeoff between sensitivity and specificity. Background signal from unmethylated and hemi-methylated DNA is measured over a titration of the MBD-APC. A similar titration with fully methylated sites will define the sensitivity of the system. A 30 fold bias in favor of fully methylated DNA over unmethylated DNA is interpreted as a success. A bias as high as 50-125 fold may be achieved (Fraga et al. (2003) Nucl. Acids Res. 31:1765-74). A set of assay responses equivalent to the unconjugated MBD will indicate that there are no adverse affects of APC conjugation.

Example 13

Methylation Detection on Native DNA Using 5-Me-dCTP

Genomic DNA is fragmented by restriction digestion and then denatured. The individual strands are then recaptured by annealing to a tagged oligonucleotide and then immobilized on a solid surface. The tagged oligonucleotide is then extended in the presence of 5-Me-dCTP to regenerate the fully methylated DNA duplex. In some cases, single stranded DNA binding protein (SSB) is be included to facilitate primer extension.

Figure 12:
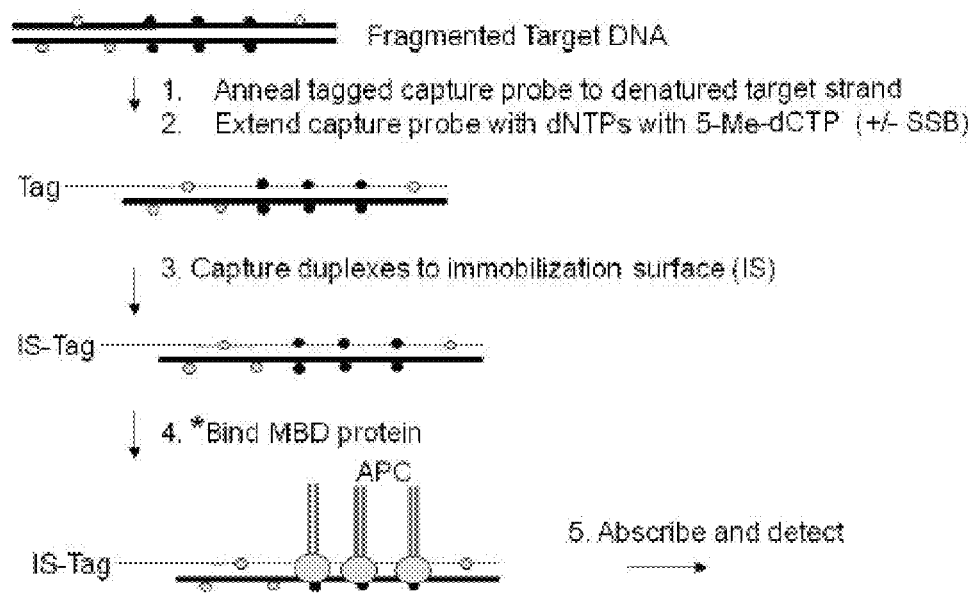
FIG. 12 shows a method for detecting methylation of a region in a target DNA fragment by capture of the target DNA to methylated target site probe.

Following extension, immobilized double-strand methylated DNA is incubated with a mCpG detector, as illustrated in FIG. 12 using an APC-mCpG-TSP. Although 5-Me-dCTP is incorporated throughout the primer extension product, the MBD polypeptide of the mCpG detector only binds at sites that contain mCpG on both strands. mCpG is detected using Abscription (FIG. 12).

In some experiments, the mCpG detector includes a mCpG-TSP that is a MBD-GST fusion polypeptide and detection utilizes an APC or HRP tagged anti-GST antibody. In other experiments, the mCpG-TSP is biotinylated and detection includes a streptavidin reagent step.

Example 14

Methylation Detection on Deaminated DNA Using 5-Me-dCTP

Figure 13:
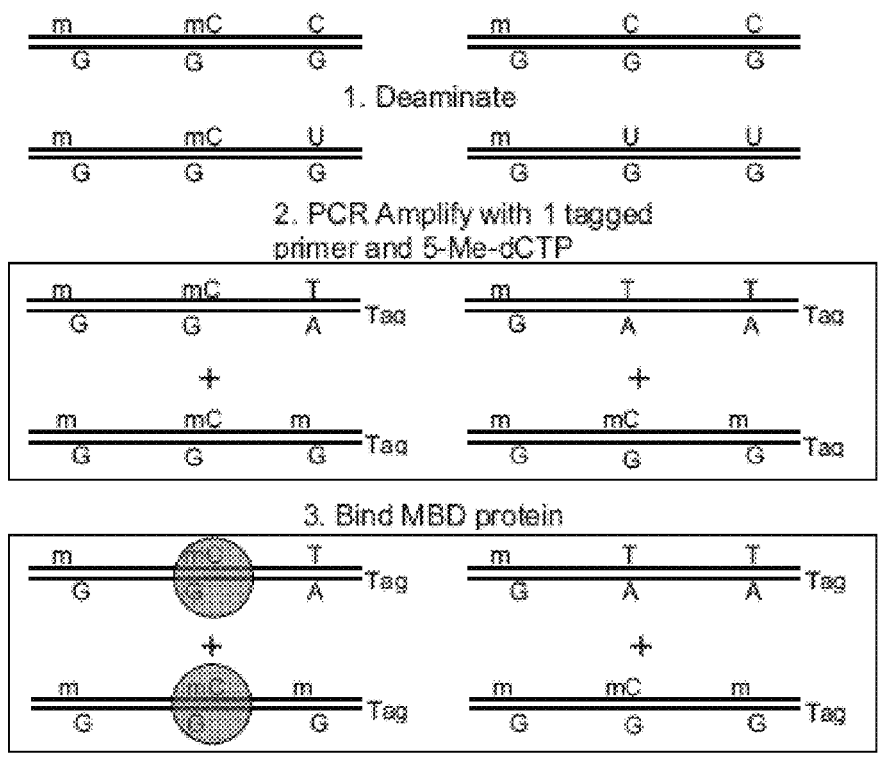
FIG. 13 illustrates capture of double strand target DNA fragments using RecA capture probe filaments.

Bisulfite treatment of methylated DNA and deamination are performed using standard procedures. As illustrated in FIG. 13 the deaminated DNA is amplified in the presence of 5-Me-dCTP by polymerase chain reaction using. Only the methylated sites in the target DNA are regenerated to contain mCpG sites on both strands.

Amplified target DNA is separated from non-amplified DNA by immobilization on a solid support and methylated CpG sites are detected using a mCpG detector.

Example 15

Figure 14:
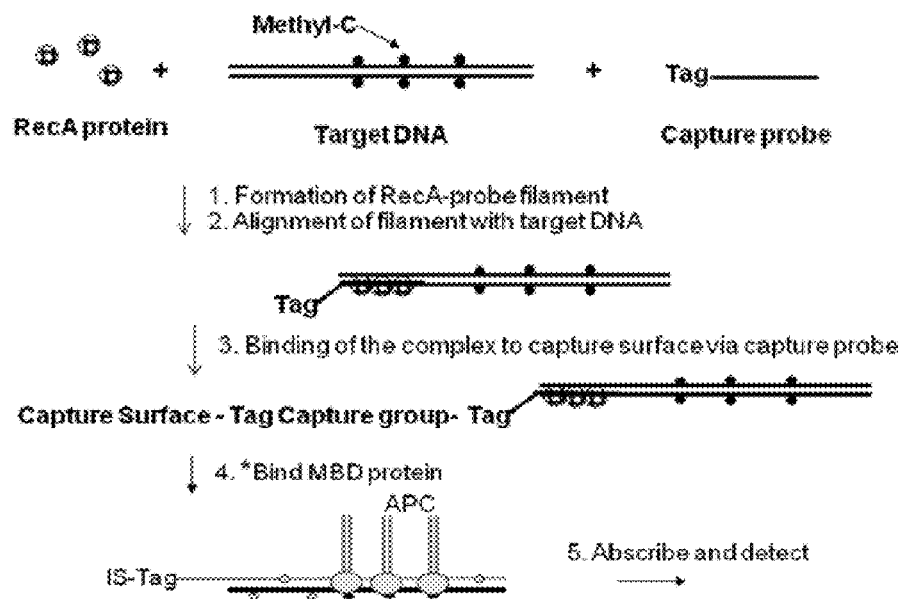
FIG. 14 is a schematic representation of a method for detecting methylation of a bisulfite treated target DNA.

RecA Mediated Double-Strand DNA Capture for Detection of Overall Methylation of Double-Strand DNA An alternative target capture procedure illustrated in FIG. 14 eliminates the need for a methylated probe by attaching the capture probe to the target molecule without a denaturation step. This approach is particularly suitable for detection of the overall level of methylation in a CpG island because the original methylation pattern does not have to be reconstructed with the use of heavily methylated probes. The RecA protein of E. coli is incubated with a biotin tagged capture probe in the presence of the nonhydrolyzable ATP analog 5'-[γ-thio]ATP. The RecA protein forms a filament on the probe DNA which aligns with the corresponding segment of the target DNA and form a stable 3-stranded structure. The 5'-affinity tag projects beyond the filament and is free to bind to streptavidin bound to a solid surface such as a bead or plate.

Following capture, the immobilized the MBD-APC fusion polypeptide reagent is bound to the immobilized target DNA. RNA polymerase and Abscription buffer are added to commence signal generation, and unlabeled Abscripts are detected by LC-MS or TLC.

What is claimed is:

1. A methylated CpG (mCpG) detector comprising an isolated methyl-CpG binding polypeptide comprising a methyl-CpG binding domain (MBD) that binds mCpG, linked to at least one abortive promoter cassette (APC), wherein the mCpG detector binds to a methylated CpG dinucleotide in a target DNA and thereby localizes the APC to the methylated CpG dinucleotide in the target DNA.

2. The mCpG detector of claim 1, wherein the methyl-CpG binding polypeptide is a fusion polypeptide further comprising an affinity tag.

3. The mCpG detector of claim 2, wherein the affinity tag is a glutathione-S-transferase (GST) domain, wherein the GST domain binds glutathione.

4. The mCpG detector of claim 2, wherein the MBD is a Methyl-CpG-Binding Protein 2 (MBD2) or Methyl-CpG-Binding Protein 2 (MeCP2) methyl binding domain.

5. The mCpG detector of claim 1, wherein the APC is covalently linked to an amino acid of the methyl-CpG-binding polypeptide.

6. A method for detecting a CpG methylated DNA fragment comprising:
   a) contacting the CpG methylated DNA fragment with the mCpG detector of claim 1, wherein the mCpG detector binds to at least one mCpG on the methylated DNA fragment, thereby forming a detector-mCpG complex;
   b) incubating the detector-mCpG complex with a solution comprising RNA polymerase, a transcription initiator and a transcription terminator, wherein at least one Abscript is synthesized from a promoter in the APC; and
   c) detecting the at least one Abscript synthesized in step (b), thereby detecting the methylated DNA.

7. The method of claim 6, wherein the at least one Abscript is a trinucleotide.

8. The method of claim 6, wherein the transcription initiator is a dinucleotide.

9. The method of claim 6, wherein the transcription terminator is an O-methyl nucleoside triphosphate.

10. The method of claim 6, wherein detecting comprises mass spectrometry.

11. A method for detecting a CpG methylated DNA fragment comprising:
   a) capturing a CpG methylated DNA fragment on a solid support;
   b) contacting the captured CpG methylated DNA fragment with the mCpG detector of claim 1, wherein the detector binds to at least one mCpG on the methylated DNA fragment, thereby forming a captured complex;
   c) incubating the captured complex with a solution comprising RNA polymerase, a transcription initiator and a transcription terminator, wherein at least one Abscript is synthesized from a promoter in the APC; and d) detecting the at least one Abscript synthesized in step (b), thereby detecting the CpG methylated DNA fragment.

12. The method of claim 11, wherein the methylated DNA fragment is a restriction fragment of genomic DNA from a clinical specimen from a subject.

13. The method of claim 12, wherein the clinical specimen is a blood, sputum, saliva, urine, semen, stool, bodily discharge, exudate, aspirate or tissue sample.

14. The method of claim 12, wherein the subject is suspected of having cancer.

15. The method of claim 14, wherein the CpG methylated DNA fragment is normally unmethylated, but is methylated in cancer.

16. The method of claim 14, wherein the cancer is selected from: lung cancer, breast cancer, colorectal cancer, prostate cancer, bladder cancer, gastric cancer, brain cancer, renal cancer, liver cancer, and leukemia.

17. The method of claim 12, wherein capturing the methylated DNA fragment on the solid support comprises:
   a) denaturing the CpG methylated DNA fragment;
   b) hybridizing the denatured CpG methylated DNA fragment to a biotinylated capture probe, wherein the capture probe is complementary to a nucleotide sequence of the CpG methylated DNA, thereby forming a biotin-CpG methylated DNA complex;
   c) contacting the biotin-CpG methylated DNA complex with a streptavidin coated solid support, thereby immobilizing the CpG methylated DNA;
   d) hybridizing the immobilized CpG methylated DNA with a mCpG probe, wherein the probe forms a duplex with at least one mCpG of the immobilized CpG methylated DNA; and
   e) removing unbound CpG methylated DNA and mCpG probe from the solid support, thereby capturing the methylated DNA fragment on the solid support.

18. The method of claim 16, wherein the mCpG probe is complementary to a CpG island.

19. The method of claim 18, wherein the cytosine of each CpG of the mCpG probe is methylated.

20. A method for detecting a CpG methylated DNA fragment comprising:
   a) annealing a biotinylated capture probe to a denatured, CpG methylated DNA fragment, thereby forming a partially duplex CpG methylated DNA fragment;
   b) contacting the partially duplex CpG methylated DNA fragment on streptavidin-coated magnetic beads, thereby capturing the CpG methylated DNA fragment;
   c) hybridizing the captured CpG methylated DNA with a mCpG probe, wherein the probe forms a duplex with at least one mCpG of the captured CpG methylated DNA fragment;
   d) contacting the captured CpG methylated DNA fragment with the mCpG detector of claim 1, wherein the detector binds to at least one duplex mCpG on the CpG methylated DNA fragment;
   e) incubating the CpG methylated DNA-bound detector of step (d) with a solution comprising RNA polymerase, a transcription initiator and a transcription terminator, wherein at least one Abscript is synthesized from a promoter in the APC; and
   f) detecting the at least one Abscript synthesized in step (e), thereby detecting the CpG methylated DNA fragment.

* * * * *

SEQUENCE LISTING

<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: synthetic linker

<400> SEQUENCE: 1

Leu Val Pro Arg Gly Ser Pro Gly Ile Ser Gly Gly Gly Gly Gly Ile
1               5                   10                  15

Arg

<210> SEQ ID NO 2
<211> LENGTH: 80
<212> TYPE: PRT
<213> ORGANISM: Mus musculus

<400> SEQUENCE: 2

Asp Arg Gly Pro Met Tyr Asp Asp Pro Thr Leu Pro Glu Gly Trp Thr
1               5                   10                  15

Arg Lys Leu Lys Gln Arg Lys Ser Gly Arg Ser Ala Gly Lys Tyr Asp
                20                  25                  30

Val Tyr Leu Ile Asn Pro Gln Gly Lys Ala Phe Arg Ser Lys Val Glu
            35                  40                  45

Leu Ile Ala Tyr Phe Glu Lys Val Gly Asp Thr Ser Leu Asp Pro Asn
        50                  55                  60

Asp Phe Asp Phe Thr Val Thr Gly Arg Gly Ser Gly Ser Gly Cys Ala
65                  70                  75                  80

```
<210> SEQ ID NO 3
<211> LENGTH: 74
<212> TYPE: PRT
<213> ORGANISM: Mus musculus

<400> SEQUENCE: 3

Glu Ser Gly Lys Arg Met Asp Cys Pro Ala Leu Pro Pro Gly Trp Lys
1               5                   10                  15

Lys Glu Glu Val Ile Arg Lys Ser Gly Leu Ser Ala Gly Lys Ser Asp
            20                  25                  30

Val Tyr Tyr Phe Ser Pro Ser Gly Lys Lys Phe Arg Ser Lys Pro Gln
        35                  40                  45

Leu Ala Arg Tyr Leu Gly Asn Ala Val Asp Leu Ser Ser Phe Asp Phe
    50                  55                  60

Arg Thr Gly Lys Met Met Pro Ser Lys Leu
65                  70

<210> SEQ ID NO 4
<211> LENGTH: 74
<212> TYPE: PRT
<213> ORGANISM: Artificial Sequence
<220> FEATURE:
<223> OTHER INFORMATION: SYNTHETIC AMINO ACID SEQUENCE

<400> SEQUENCE: 4

Glu Ser Gly Lys Arg Met Asp Asp Pro Ala Leu Pro Pro Gly Trp Lys
1               5                   10                  15

Lys Glu Glu Val Ile Arg Lys Ser Gly Leu Ser Ala Gly Lys Ser Asp
            20                  25                  30

Val Tyr Tyr Phe Ser Pro Ser Gly Lys Lys Phe Arg Ser Lys Pro Gln
        35                  40                  45

Leu Ala Arg Tyr Leu Gly Asn Ala Val Asp Leu Ser Ser Phe Asp Phe
    50                  55                  60

Arg Thr Gly Lys Met Met Pro Ser Lys Leu
65                  70
```